(12) United States Patent
Kovak et al.

(10) Patent No.: US 7,212,854 B2
(45) Date of Patent: May 1, 2007

(54) NEURO-MUSCULAR STIMULATTOR CHANNEL SEQUENCER

(76) Inventors: Stanley J. Kovak, 2015 N. 74th Ct., Elmwood Park, IL (US) 60707; Ryan W. Kingsbury, 6730 Tortoise Run Ct., North Fort Meyers, FL (US) 33917

( * ) Notice: Subject to any disclaimer, the term of this patent is extended or adjusted under 35 U.S.C. 154(b) by 449 days.

(21) Appl. No.: 10/375,550

(22) Filed: Feb. 26, 2003

(65) Prior Publication Data
US 2004/0167585 A1  Aug. 26, 2004

(51) Int. Cl.
*A61N 1/04* (2006.01)
(52) U.S. Cl. .............................. 607/2; 607/46
(58) Field of Classification Search ..................... None
See application file for complete search history.

(56) References Cited

U.S. PATENT DOCUMENTS 5,562,718 A * 10/1996 Palermo ...................... 607/46
6,564,103 B2 * 5/2003 Fischer et al. ................. 607/59
2003/0045992 A1 * 3/2003 Northrop ..................... 607/139

OTHER PUBLICATIONS

NeuroTech NT2000 Operators Instruction Manual.
Neurotech NT 2000 Patient Instruction Manual.

* cited by examiner

*Primary Examiner*—Robert E. Pezzuto
*Assistant Examiner*—Kristen Mullen
(74) *Attorney, Agent, or Firm*—McAndrews, Held & Malloy, Ltd.

(57) ABSTRACT

A neuro-muscular electrical stimulator includes a signal generator that generates at least one neuro-muscular stimulation signal and a programmable channel sequencer having six or more output channels. The channel sequencer couples the stimulation signal to the sequencer output channels in a predetermined sequence. A programmer that communicates with the sequencer allows a physician to individually program, for each sequencer output channel, the length of the time period during which the stimulation signal is coupled to the output channel so as to provide a patient specific therapy prescription.

35 Claims, 19 Drawing Sheets

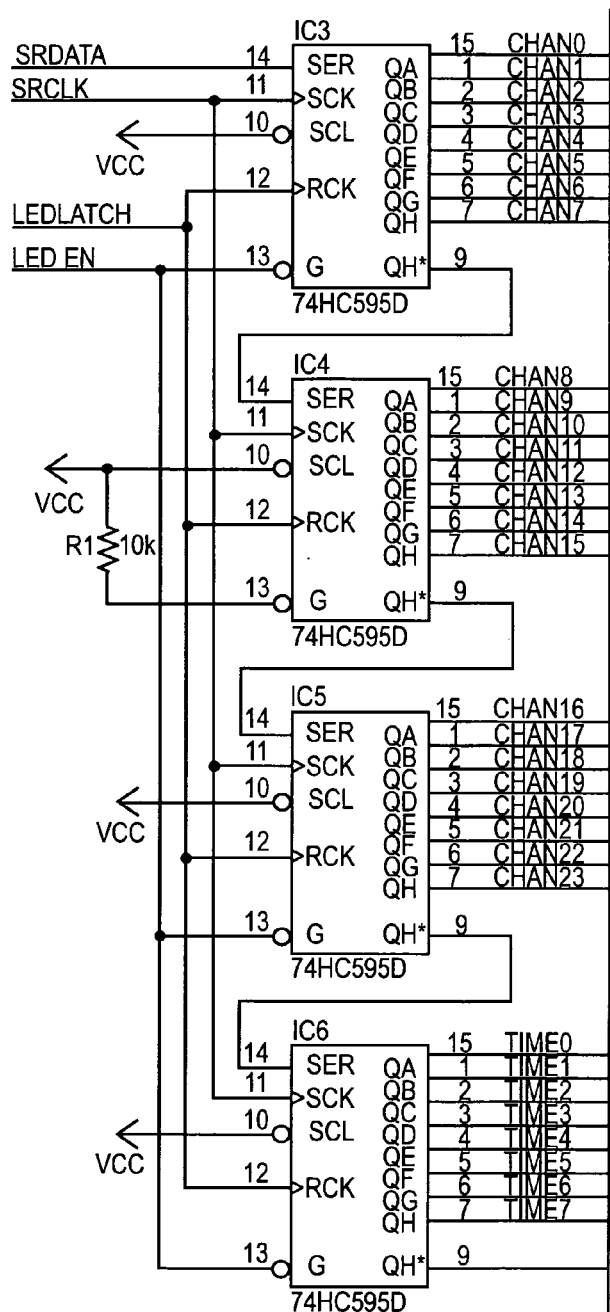
FIG. 23a
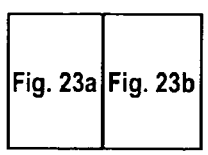
FIG. 23
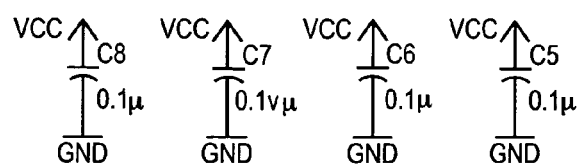

NEURO-MUSCULAR STIMULATTOR CHANNEL SEQUENCER

CROSS-REFERENCE TO RELATED APPLICATIONS

N/A

STATEMENT REGARDING FEDERALLY SPONSORED RESEARCH OR DEVELOPMENT

N/A

BACKGROUND OF THE INVENTION

The present invention is directed to a portable muscle/nerve stimulation system and more particularly to such a system having a programmable channel sequencer with a sufficient number of output channels to which electrodes are coupled to allow a complete programmed therapy to be performed without requiring the electrodes to be moved.

Portable neuro-muscular electrical stimulators have been known to provide a stimulation signal on two channels where each channel is coupled to a pair of electrodes that are attached to the patient's skin so as to stimulate a muscle or nerve. One such stimulator is the NeuroTech NT2000 manufactured and/or sold by Bio-Medical Research Ltd. The stimulation signal of the NT2000 has a contraction cycle and a relaxation cycle, each cycle formed of a number of pulses. The NT2000, in one mode, provides a stimulation signal on each of the two channels at the same time so that the contraction and relaxation cycles coincide but the individual pulses on the two channels are offset. In another mode, the stimulation signal alternates between the two channels. Various parameters of the NT2000 are programmable including frequency, pulse width, contraction cycle, length, relaxation cycle length, ramp up period, ramp down period, amplitude limit and a delay period between the ramp up time on the two channels. The treatment time for one therapy session is also programmable. Upon termination of the treatment time, the unit must be turned off and then turned on to start a new therapy session.

One of the main problems with known neuro-muscular stimulators is that they have a very limited number of output channels. As such, in one therapy session, the electrodes may have to be manually moved a number of times so as to treat different muscles/nerves. Moreover, in many cases, each time the electrodes are moved, the stimulator has to be reprogrammed because the treatment time for various muscles/nerves varies. Known stimulators with more than one channel are still not flexible enough for many applications because the treatment time for each channel is not individually programmable. Instead, it is only the total time that the unit is generating signals that is programmable.

For facial muscle toning, the disadvantages of prior neuro-muscular stimulators is particularly apparent. For facial muscle toning, a large number of electrodes of small diameter is desired. Moreover, the length of time that a given electrode pair should be active can vary considerably from one electrode pair position to another electrode pair position for a single patient as well as from patient to patient. Therefore, one therapy prescription is not suitable for all patients.

BRIEF SUMMARY OF THE INVENTION

In accordance with the present invention, the disadvantages of prior neuro-muscular stimulators have been overcome. The neuro-muscular stimulator of the present invention has a sufficient number of output channels to which electrodes are coupled to allow a complete programmed therapy to be performed without requiring the electrodes to be moved or the unit to be reprogrammed during a given therapy session. Moreover, the stimulator of the present invention is portable and can be used at home by a patient after it is programmed for the patient by a physician.

More particularly, the neuro-muscular stimulator of the present invention includes a signal generator for providing at least one neuro-muscular stimulation signal and a channel sequencer having a number of output channels greater in number than the stimulation signals generated by the neuro-muscular stimulation signal generator. Each of the sequencer output channels is capable of providing an output stimulation signal to a pair of electrodes. The channel sequencer couples one stimulation signal from the signal generator to a selected group of output channels of the channel sequencer in a predetermined sequence wherein the time period during which the stimulation signal is coupled to a sequencer output channel in the selected group is individually programmable for each output channel in the group. The channel sequencer automatically switches the one stimulation signal from a current sequencer output channel in the selected group to the next selected output channel in the sequence in response to the expiration of the programmable period of time associated with the current sequencer output channel.

In a preferred embodiment of the present invention, the signal generator generates at least two stimulation signals and the channel sequencer couples the two signals to different groups of channel outputs in parallel so as to reduce the total therapy time.

The neuro-muscular signal generator and channel sequencer may be contained in a single portable housing to form an integrated unit. Alternatively, the neuro-muscular signal generator and the channel sequencer can be contained in two separate housings or modules where the electronics in one housing communicates with electronics in the other housing. In a preferred two housing embodiment, the housings of the signal generator and the channel sequencer mate so as to form one portable, unitary device.

The system of the present invention also includes a programming unit that communicates with the neuro-muscular stimulator to program the time periods during which the stimulation signal is to be coupled to the sequencer output channels in a selected group individually for each output channel in the selected group.

These and other advantages and novel features of the present invention, as well as details of an illustrated embodiment thereof, will be more fully understood from the following description and drawings.

DETAILED DESCRIPTION OF THE INVENTION

Figure 1:
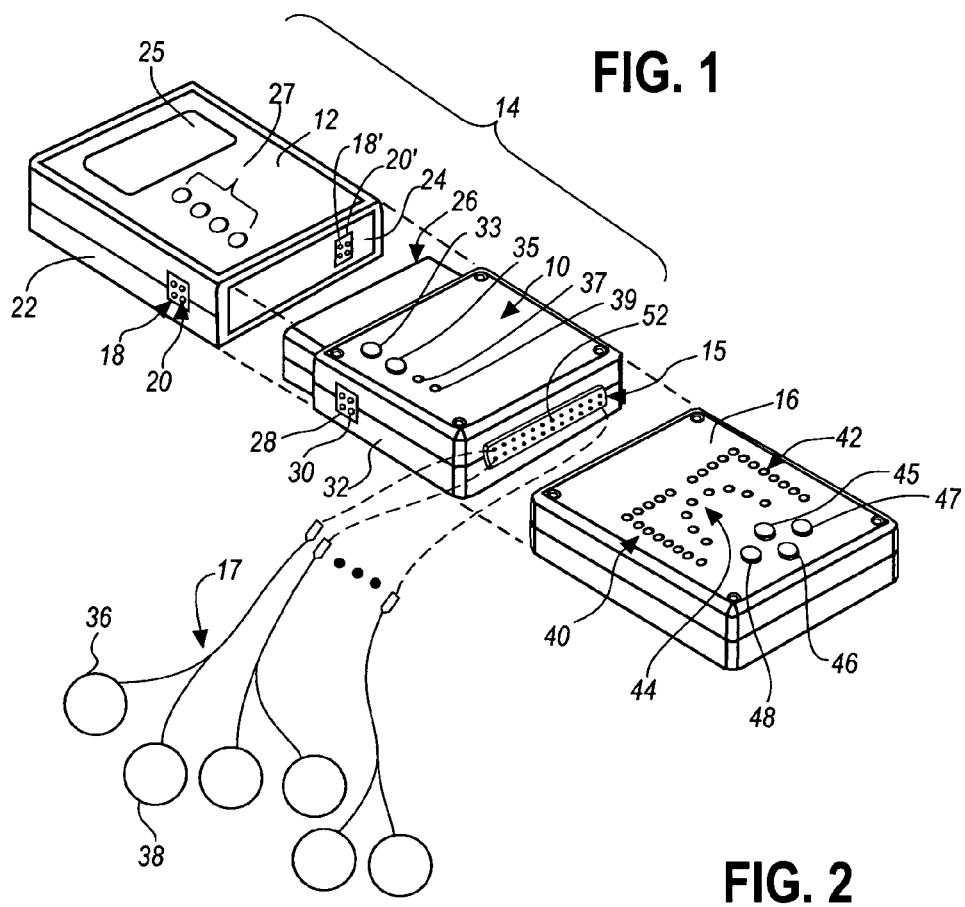
FIG. 1 is a perspective view of the neuro-muscular stimulator of the present invention including a signal generator module, a channel sequencer module to which electrodes are coupled and a programming module.

The neuro-muscular stimulator of the present invention, as shown in FIG. 1 includes a channel sequencer module 10 and a signal generator module 12 which when mated together form a unitary patient activated device 14. The channel sequencer 10 couples a neuro-muscular stimulation signal generated by the signal generator 12 to each of a number of output channels 15 in a predetermined sequence and for a programmable period of time. Each of the output channels 15 is connectable to a pair of electrodes, such as the electrode pair 17 to apply the stimulation signal to the patient. The channel sequencer 10 or the device 14 may be programmed with a therapy prescription for a particular patient by a physician using a programmer 16 as discussed in detail below.

The signal generator 12 may generate a neuro-muscular stimulation signal on one output channel or the generator 12 may include a multiplexor or the like to generate a neuro-muscular stimulation signal on two or more output channels of the generator 12. A suitable neuro-muscular stimulation signal generator is a NeuroTech NT2000 manufactured by Bio-Medical Research Ltd. which has two output channels 18 and 20 positioned on a side 22 of the signal generator 12. Alternatively, the output channels 18' and 20' can be positioned on a base 24 of the signal generator module 12 to which the channel sequencer 10 mates. The signal generator 12 includes a display 25 and control buttons 27 for controlling the signal generator 12 independently of the channel sequencer 10 if desired. In this embodiment, the signal generator 12 may also be programmed independently of the channel sequencer 10 by a suitable programming device so as to define the type of stimulation signal generated. The channel sequencer module 10 has a top 26 that mates with the base 24 of the signal generator module 12 so that the two modules form one portable device 14. The modules 10 and 12 can be electrically connected through the base 24 (via channel outputs 18', 20') of the signal generator module 12 and the top 26 (via respective channel inputs not shown) of the channel sequencer 10 and/or by a cable coupling the two channel outputs 18 and 20 of the signal generator 12 to two channel inputs 28 and 30 on the side 32 of the channel sequencer 10.

The channels sequencer 10 as discussed in detail below, couples the stimulation signal received from one of the output channels, for example output channel 18, of the signal generator 12 to a number of output channels 15 in a first group or bank, hereinafter referred to as bank A, in a predetermined sequence. The time period during which the stimulation signal is coupled to an output channel in bank A is individually programmable for each of the bank A output channels. Similarly, the channel sequencer 10 couples the stimulation signal received from the other output channel 20 of the signal generator 12 to a number of output channels 15 in a second group or bank, hereinafter referred to as bank B, in a predetermined sequence. The time period during which the stimulation signal is coupled to an output channel in bank B is individually programmable for each of the bank B output channels as well. In a preferred embodiment, the bank B output channels are activated in parallel with the bank A output channels so as to reduce the total time to complete a given therapy. It should be noted that one therapy session encompasses the activation of all of the non-disabled output channels for the channels' programmed time periods.

In an alternative embodiment, the time periods associated with various output channels can be tied together so that when one output channel is programmed for a particular time period, the other output channels tied thereto are automatically set to have the same programmed time period. For example, the time periods associated with the output channels in bank B may be tied to corresponding output channels in bank A. In this example, the time period associated with the first output channel in the bank B sequence may be automatically set equal to the time period programmed for the first output channel in bank A sequence; the time period associated with the second output channel in the bank B sequence may be automatically set equal to the time period programmed for the second output channel in the bank A sequence; and so on. It should be apparent that, output channels in the same bank can be tied together as well as output channels in different banks.

The channel sequencer 10 has a power on button 33 to turn on the sequencer and a pause/off button 35. Depending upon the length of time that the button 35 is held down, the sequencer 10 will either enter a pause state or turn off. LEDs 37 and 39 provide feedback when lit, respectively indicating that the sequencer 10 is in a pause state or battery charge in progress state. The channel sequencer 10 should have at least six output channels for the stimulation signal so as to be able to treat six muscles/nerves in one therapy session. In a preferred embodiment for facial muscle toning, twenty-four output channels 15 are provided on the channel sequencer 10 so as to connect to twenty-four pairs of electrodes 17. For facial muscle toning, the diameter of the electrodes, such as electrodes 36 and 38 of the electrode pair 17, should be one inch or less and preferably on the order of three quarters of an inch or less.

The programmer 16 allows the physician to program a therapy prescription into the patient activated device 14 for a particular patient. For example, for facial muscle toning, the physician can map the electrodes to specific locations on the patient's face so that the first electrode pair coupled to the first output channel, designated channel zero for the firmware, is placed at a first facial location; the second electrode pair coupled to the second output channel, designated channel one, is placed at a second facial location and so on up through the twenty-fourth electrode pair coupled to the twenty-fourth output channel, designated channel twenty-three. Once the physician maps the channel outputs to particular electrode placements, the physician can use the programmer 16 to program for each output channel, a time period during which the channel sequencer 10 is to couple the stimulation signal to that particular output channel. The physician can thereby prescribe for each muscle/nerve to be stimulated an individual stimulation time period. For facial muscle/nerve stimulation, this is important because not all muscles/nerves on the face will require the same amount of stimulation. It is noted that the physician can use less than all of the twenty-four electrode pairs for a patient by disabling the output channels that are not to be used. This is done by programming the time period for a particular output channel to zero. In this manner, the physician determines the sequence in which various output channels are activated.

The patient programmer has twenty-four LEDs 40, 42 each LED associated with a particular output channel of the channel sequencer 10. The LEDs 40 are associated with the output channels zero-eleven in bank A of the device of the channel sequencer 10; whereas, the LEDs 42 are associated with respective output channels twelve through twenty-three in bank B of the channel sequencer 10. The programmer 16 also includes a number of LEDs 44, each associated with a particular time period that can be programmed into the channel sequencer 10 for the output channels. Four control buttons 45–48 are used by the physician to select a particular output channel to be programmed and to select a particular time period, for that output channel. For example, the button 45 is used to increment the selectable time period and light the associated LED 44; whereas the button 46 is actuable to decrease the selectable time period and change the LED 44 that is lit. The button 47 is actuable by a physician to select the next output channel and light the associated LED 40, 42; whereas the button 48 is actuable to select the previous output channel and associated LED 40, 42. The first time channel that is selectable is a time period of zero which means that the channel is disabled. After that, the selectable time periods associated with each of the LEDs 44 start at one minute and are incremented by 30 seconds up through 7 minutes.

The programmer 16 has an electrical connector 50 that mates with particular pins, as discussed below, of the connector 52 of the channel sequencer. The connector 52 also includes the twenty-four output channels 15 of the patient activated device 14. Instead of a direct electrical connection, the programmer 16 can communicate with the patient activation device 14 via telemetry, such as by R.F. communications or I.R. communications, if desired.

Figure 2:
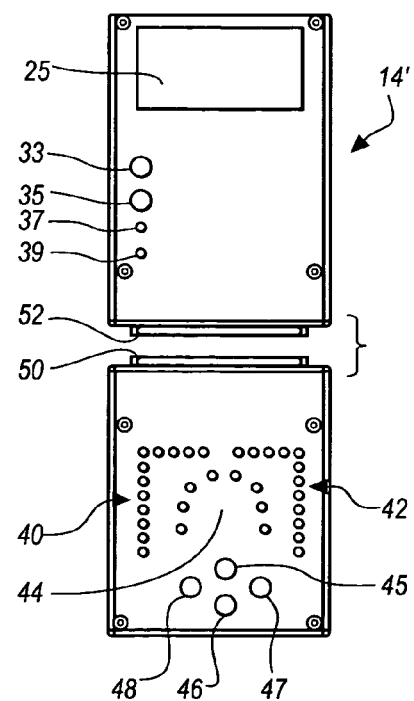
FIG. 2 is a top view of an alternative embodiment of the neuro-muscular stimulator of the present invention having a single housing for the signal generator and channel sequencer and illustrating the programmer of FIG. 1.

The programmer 16 can also be used with a patient activated device 14' as shown in FIG. 2. In FIG. 2, the device 14' contains the signal generator 12 and channel sequencer 10 in a single housing. In this embodiment, the programmer 16 preferably programs both the type of stimulation signal generated and the time periods associated with the output channels 15. Further, instead of the LEDs 40, 42 and 44, the programmer can provide visual feedback via the display 25. It is noted that the display 25 can also provide feedback information to a patient when the device 14' is in use. Such feedback information may include an identification of the currently active channels and/or the number of output channels finished or the number of output channels left and/or the length of time left until the therapy is done.

Figure 3:
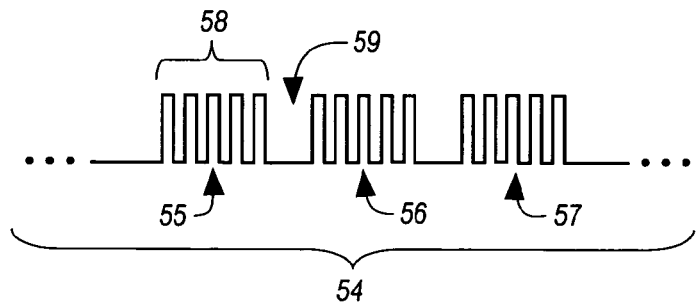
FIG. 3 is an illustration of a stimulation signal.

An example of a neuro-muscular stimulation signal 54 generated by the signal generator 12 and coupled to an output channel of the channel sequencer 10 is illustrated in FIG. 3. The neuro-muscular stimulation signal 54 in this example includes a series of pulse groups such as shown at 55, 56 and 57 wherein each pulse group represents a contraction cycle. The amplitudes of the pulses in a contraction cycle 58 of the stimulation signal 54 may be constant. Alternatively, the amplitude of the pulses may ramp up to a particular level. If desired, a relaxation cycle can include pulses that ramp down to an idle period depicted at 59. It is noted that the idle period 59 can be considered part of a relaxation cycle. In a preferred embodiment as described below, the signal generator 12 includes a multiplexor or the like to generate two neuro-muscular stimulation signals on the respective output channels 18 and 20 at the same time. In this example, the contraction cycles of both neuro-muscular stimulation signals may substantially coincide, however, typically, the individual pulses of one signal are offset from the pulses in the other signal.

Figure 4:
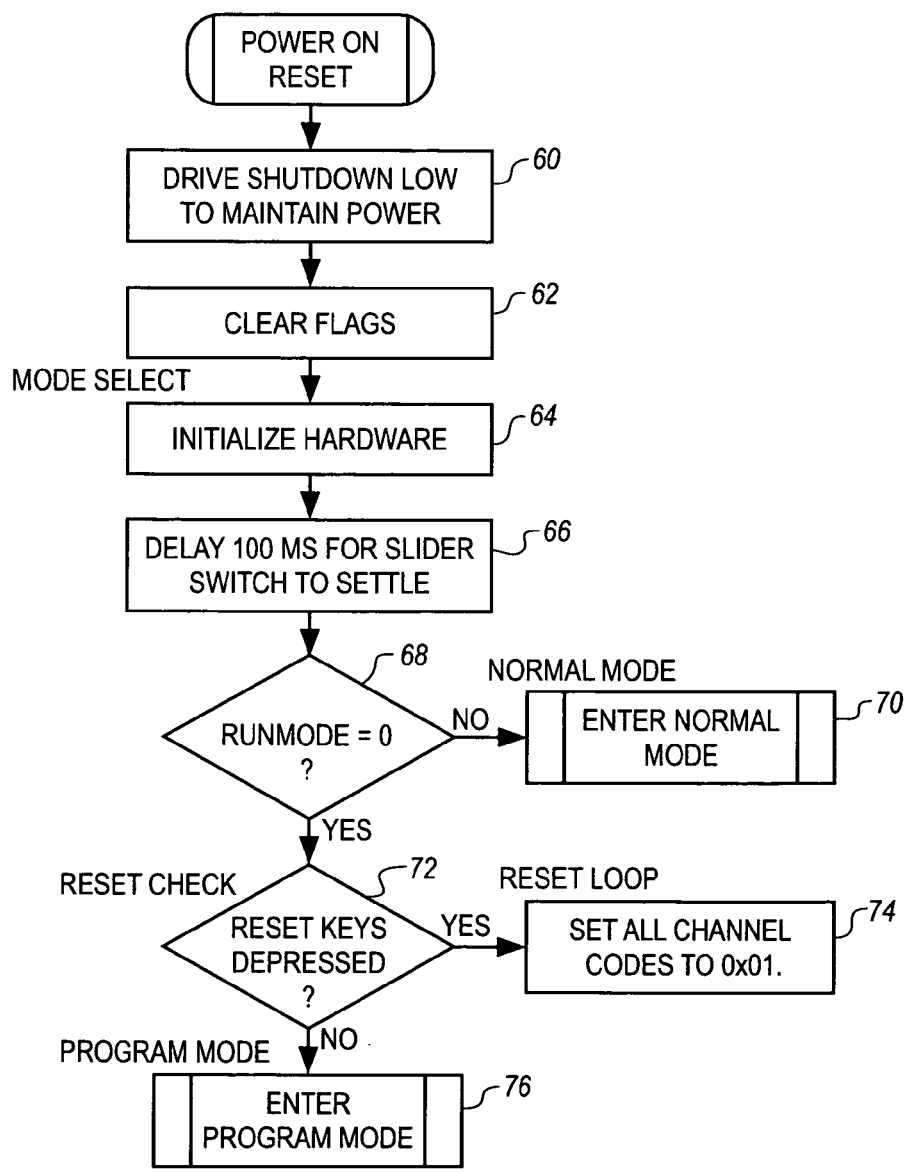
FIG. 4 is a flow chart illustrating a start up routine for the channel sequencer.
Figure 5:
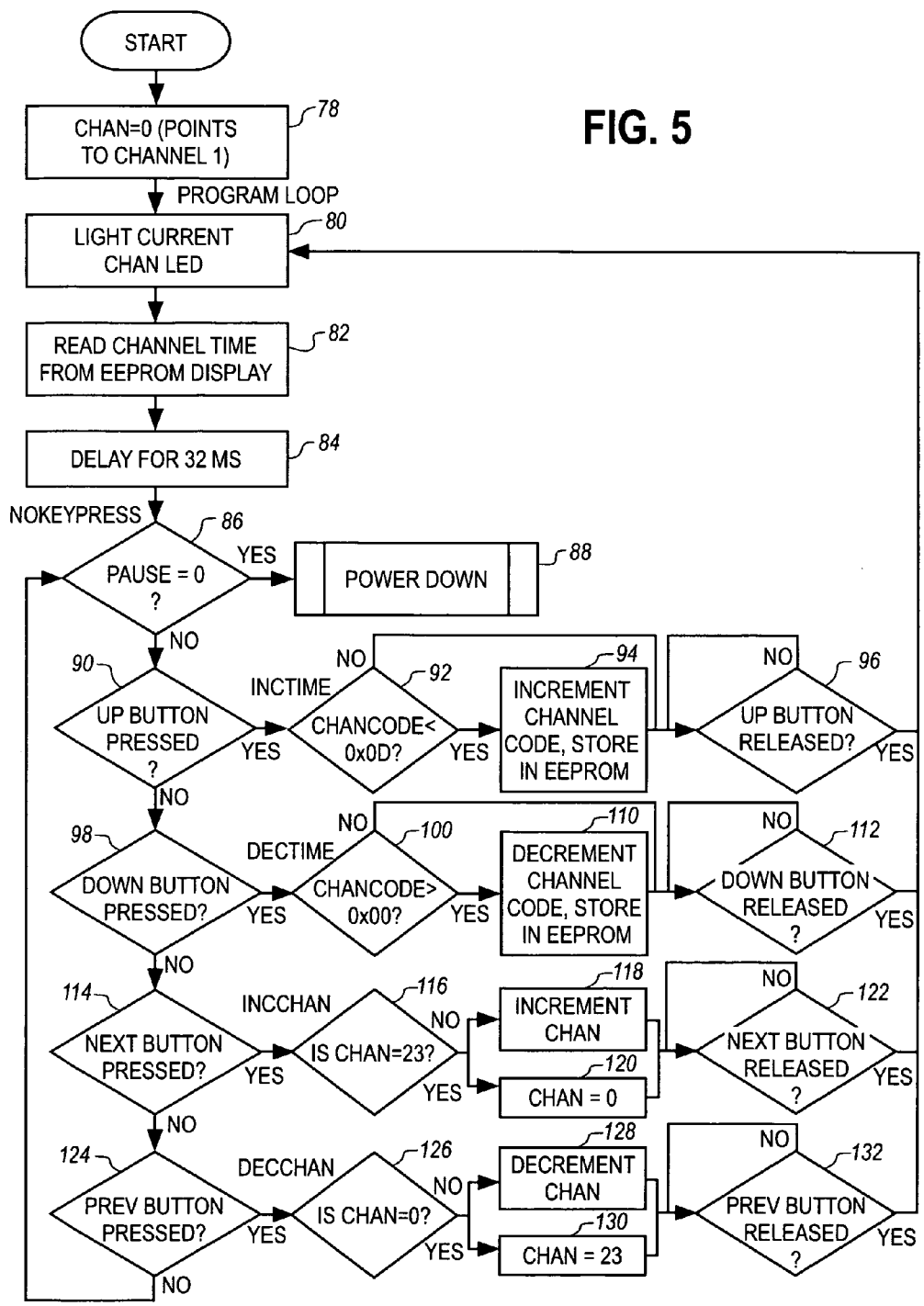
FIG. 5 is a flow chart illustrating the programming mode depicted in FIG. 4.
Figure 13:
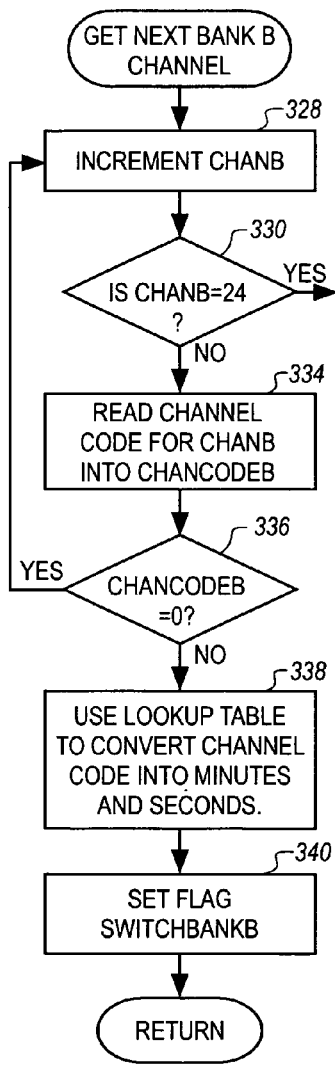
FIG. 13 is a flow chart illustrating a routine to get the time periods for a second bank of channels.
Figure 14:
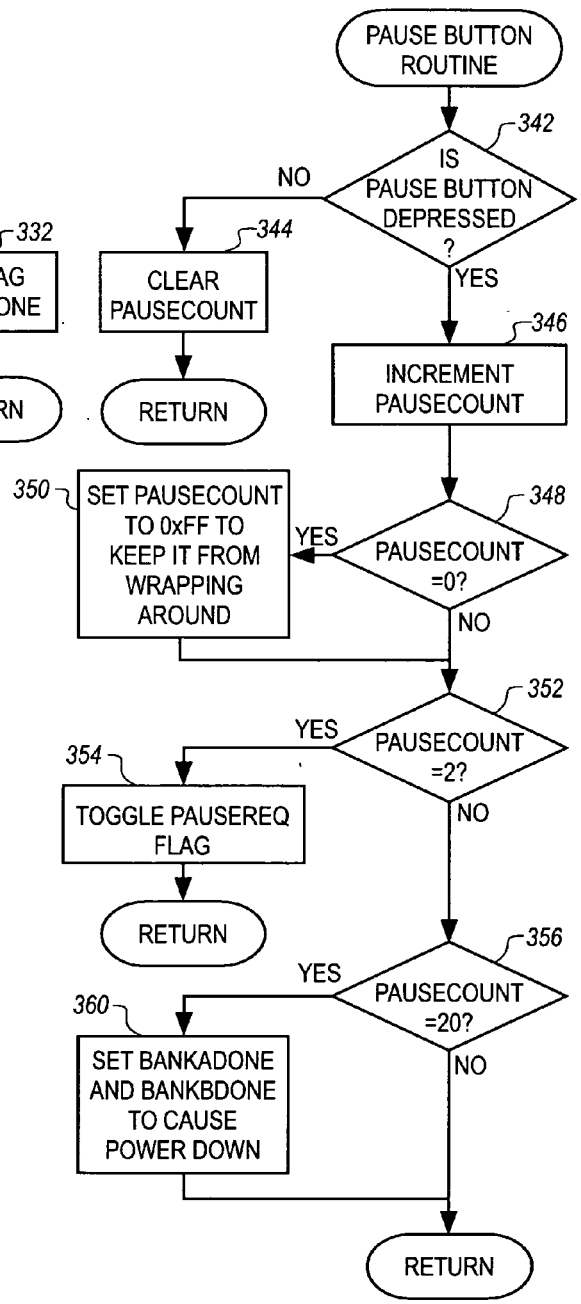
FIG. 14 is a flow chart illustrating a pause button routine.
Figure 15:
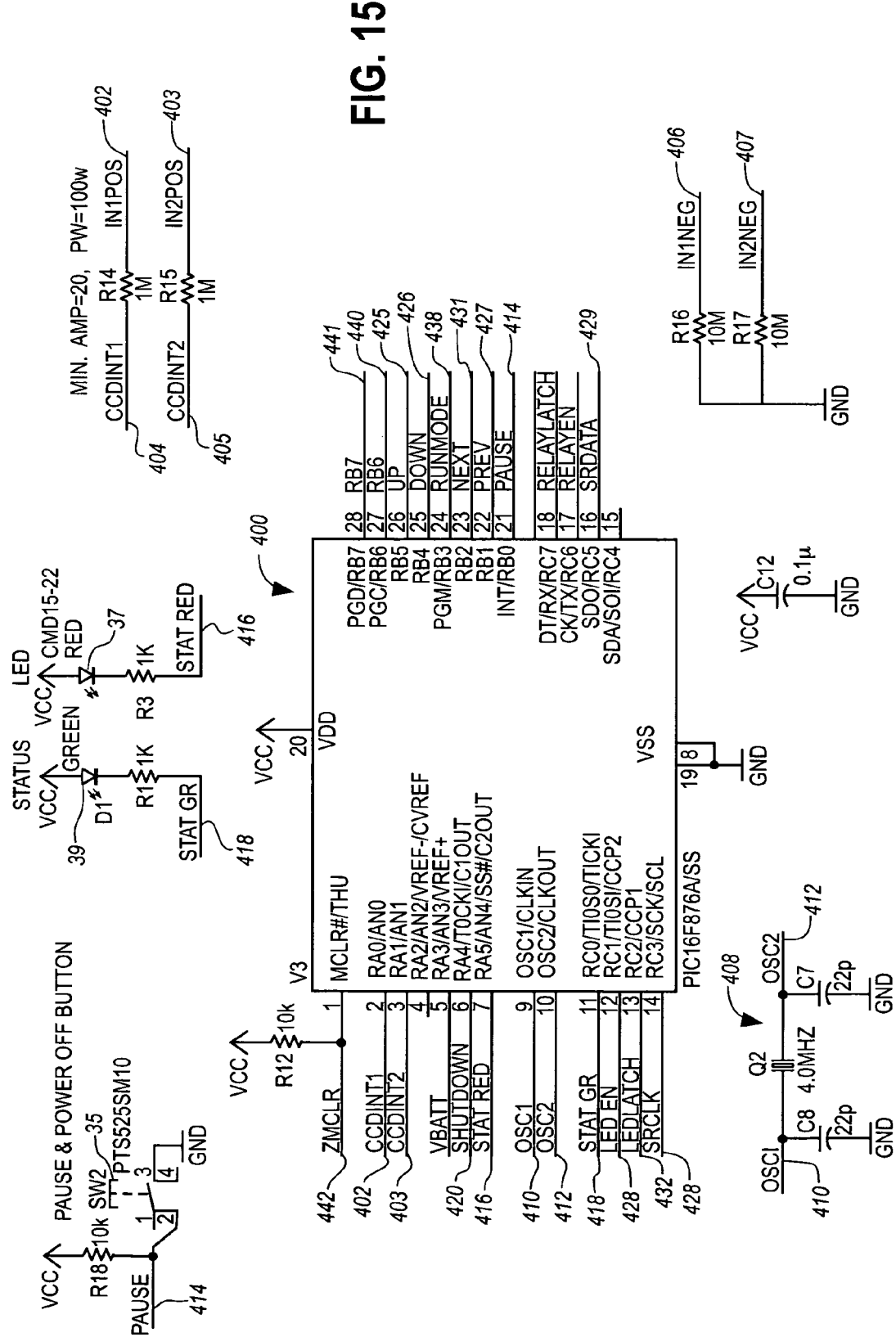
FIG. 15 is a schematic diagram of a microcontroller circuit for the channel sequencer of FIGS. 1 and 2.

The channel sequencer 10 as discussed below with regard to FIG. 15 is a microcontroller based unit wherein the microcontroller includes a processor and memory. FIGS. 4–14 illustrate the various software routines implemented by the microcontroller to control the channel sequencer 10. FIG. 4 illustrates a main software routine to initialize the sequencer. Upon pressing the power on button 33 of the sequencer 10, the microcontroller at block 60 drives a shutdown line 420 low so as to maintain power on. Thereafter, the microcontroller clears various flags at block 62. At block 64, the microcontroller initializes hardware for mode selection, i.e. the normal operating mode of the patient activated device or a program mode to allow the channel sequencer 10 to be programmed by a programmer 16. The microcontroller at block 66 then provides a 100 ms delay for switch settling. At block 68, the microcontroller determines whether a Runmode line 438 has been pulled to zero by the programmer 16 being attached to the sequencer 10. If not, the microcontroller, at block 70, enters the software routine depicted in FIG. 6 for the normal mode initialization. If the Runmode value is determined to be zero at block 68, the microcontroller proceeds to block 72 to determine whether a reset key has been pressed. If so, the microcontroller at block 74 sets all of the channel codes to a code 0x01 which designates a default value of one minute. It should be apparent that other default values may be used. For example, a default value of 0x00 will disable the channels. If a reset key has not been pressed, the microcontroller proceeds from block 72 to block 76 to enter the programming mode which is depicted in FIG. 5.

In the programming mode, shown in FIG. 5, the microcontroller starts at block 78 with the first channel being designated channel zero for the firmware. The microcontroller at block 80 lights the channel LED 40 associated with the current channel. At block 82, the microcontroller reads the channel time associated with the current channel and based on values stored in the microcontroller's non-volatile memory, the microcontroller lights the LED 44 on the programmer 16 associated with the stored channel time for the current channel. After a delay of 32 ms at block 84, the microcontroller proceeds to block 86 to determine whether the pause line 414 is set equal to 0. If the pause line 414 is set equal to 0, the microcontroller at block 88 implements a power down routine. If the pause line 414 is not set equal to 0, the microcontroller proceeds from block 86 to block 90. At block 90, the microcontroller determines whether the up button 45 on the programmer 16 has been pressed. If the up button has been pressed, the microcontroller at block 92 determines whether the current channel's channel code, representing a time period, is less than 0x0D which designates the maximum programmable time period of 7 minutes. If the channel code is less than 0x0D, the microcontroller at block 94 increments the channel code to the next value which is stored in the memory. The microcontroller then determines at block 96 whether the up button has been released and if so, proceeds back to block 80. And at block 82, the microcontroller lights the LED 44 associated with the current time period. If the microcontroller determines at block 98 that the down button 46 on the programmer 16 has been pressed, the microcontroller proceeds to block 100. At block 100, the microcontroller determines whether the current channel's channel code representing a time period as indicated by the lit LED 44, is greater than 0x00. If so, the microcontroller at block 110 decrements the channel code to the immediately preceding channel code stored in the memory. At block 112 the microcontroller determines whether the down button 46 has been released and if so, the microcontroller returns to block 80 and block 82 where the LED associated with the decremented time period is lit.

If the microcontroller determines at block 114 that the next button 47 has been pressed on the programmer 16, the microcontroller determines at block 116 whether the channel is equal to 23, designating the last or twenty-fourth output channel of the channel sequencer 10. If the current channel is not the last channel, at block 118, the microcontroller increments the channel number and at block 122 determines whether the next button has been released. When the next button has been released as determined at block 122, the microcontroller proceeds back to block 80 and lights the LED associated with the next channel. If at block 116 the microcontroller determines that the current channel number is equal to 23, i.e. representing the last or twenty-fourth output channel, the microcontroller proceeds to block 120 to set the channel number back to 0 i.e., pointing to the first output channel of the channel sequencer 10. From block 120, the microcontroller proceeds to block 122 as discussed above. If the microcontroller determines at block 124, that the previous button 48 on the programmer 16 has been pressed, the microcontroller proceeds to block 126 to determine whether the current channel number designation is 0. If the current channel designation is 0, the microcontroller at block 130 sets the current channel designation to 23 i.e., pointing to the last or twenty-fourth output channel of the channel sequencer 10 at block 130. If the channel designation is determined to be other than 0 at block 126, the microcontroller proceeds to block 128 to decrement the channel number. Thereafter, the microcontroller proceeds to block 132 to determine when the previous button 48 has been released. When the previous button has been determined to be released at block 132, the microcontroller returns to block 80 to light the LED associated with the decremented channel number. In this manner, the channel sequencer is responsive to the programmer 16 so that a physician can program time periods for each individual output channel in banks A and B of the channel sequencer 10 so as to provide a therapy prescription for a patient.

Figure 6:
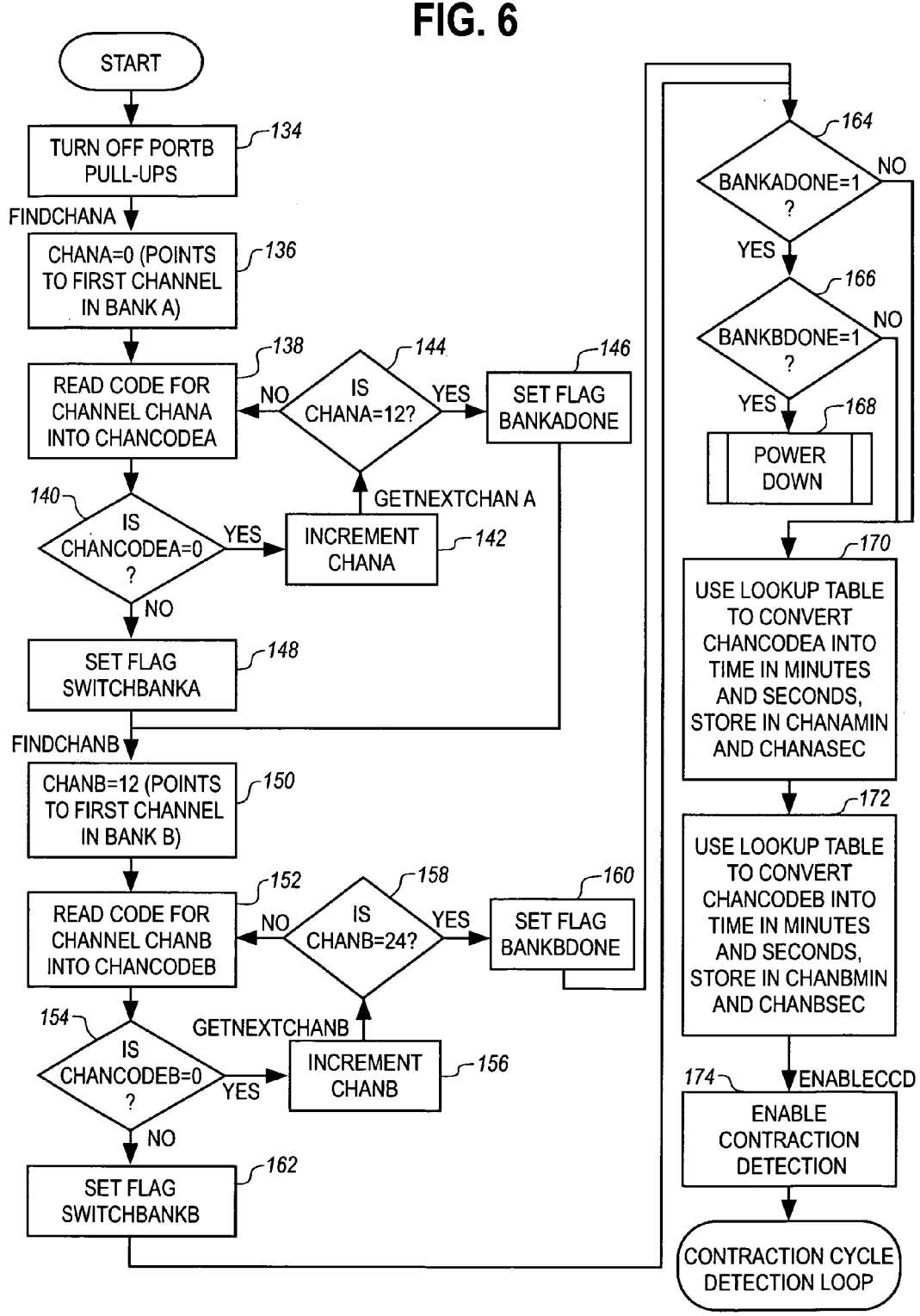
FIG. 6 is a flow chart illustrating the initialization routine for the normal mode depicted in FIG. 4.

The initialization for the normal mode of operation is depicted in FIG. 6. At block 134, the microcontroller turns, off its port B pull up resistors. The microcontroller at block 136 sets a pointer chanA equal to 0 so as to point to the first channel in bank A. Then at block 138, the microcontroller reads the code representing the time period for the current channel, chanA, into chancodeA. If chancodeA is set equal to 0 indicating that the current channel is disabled, the microcontroller proceeds to block 142 to increment the pointer chanA to the next output channel. The microcontroller at block 144 determines whether the current channel, chanA, is equal to 12, and if not, the microcontroller returns to block 138 to read the time period code for the new chanA into chancodeA. Thereafter, the microcontroller returns to block 142 to determine whether the code representing the time period for this output channel is 0 so that the channels is disabled. The blocks 138, 140, 142 and 144 are looking for the first output channel in bank A for which the time period code is not zero. That is, the microcontroller is looking for the first output channel that is not disabled. When that output channel is found, the microcontroller proceeds to block 148 to set a flag, switchbankA equal to 1. If the microcontroller has not found an output channel in bank A that is not disabled, the microcontroller proceeds from block 144 to block 146 to set a flag bankAdone. From blocks 146 or block 148, the microcontroller proceeds to block 150 to find the first channel in bankB that is not disabled. At block 150, the microcontroller sets a bankB pointer, chanB, equal to 12 so as to point to the first channel in bankB. Thereafter, at block 152, the microcontroller reads the code representing the time period for the current bank B channel, chanB, into chancodeB. At block 154, the microcontroller determines whether chancodeB is equal to 0 indicating that the current channel is disabled. If so, the microcontroller proceeds to block 156 to increment the pointer chanB to the next output channel. If the microcontroller determines that chanB is not equal to 24 at block 158, the microcontroller returns to blocks 152 and 154 to read the code representing the time period for the incremented output channel, chanB, into chancodeB and to determine if that code is equal to 0 indicating that the channel is disabled. When the microcontroller finds the first channel in bankB that is not disabled as determined at block 154, the microcontroller proceeds to block 162 to set the flag switchbankB. If the microcontroller determines at block 158 that all of the output channels in bankB are disabled, the microcontroller proceeds to block 160 to set the flag bankBdone. The microcontroller proceeds from either block 160 or 162 to block 164.

At block 164, the microcontroller determines whether the flag bankAdone was set equal to 1 at block 146 indicating that all of the output channels in bankA have been disabled. If so, the microcontroller proceeds to block 166 to determine whether the flag bankBdone was set equal to 1 at block 160 indicating that each of the output channels in bankB was disabled also. If so, the microcontroller proceeds to block 168 to power down the sequencer 10. If the bankAdone flag was not set at block 146 or the bankBdone flag was not set at block 160, the microcontroller proceeds from respective blocks 164 or 166 to block 170. At block 170, the microcontroller utilizes a look up table to convert the code in chancodeA associated with the first non-disabled output channel in bankA into time as represented in minutes and seconds. At block 170, the microcontroller stores the number of minutes for which the first channel in bankA is to be active in chanAmin, whereas the seconds are stored in chanAsec. Thereafter at block 172, the microcontroller uses the look up table to convert the code stored in chancodeB for the first non-disabled output channel in bankB into time in minutes and seconds, wherein the minutes are stored in chanBmin and the time in seconds is stored in chanBsec. The microcontroller thereafter at block 174 implements an enable contraction detection routine shown in FIG. 11 and thereafter, the microcontroller proceeds to implement a contraction cycle detection routine shown in FIG. 7.

Figure 7:
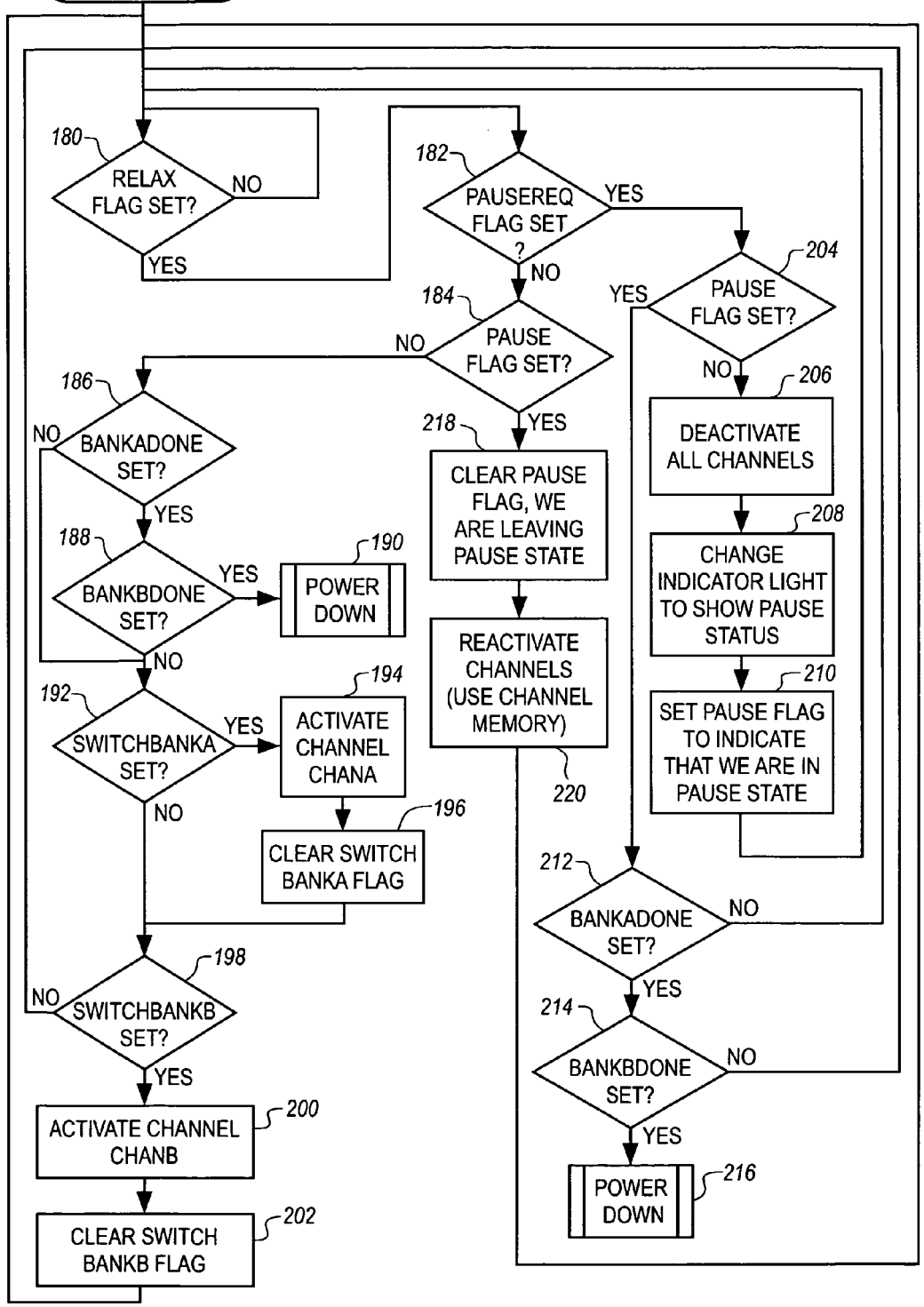
FIG. 7 is a flow chart illustrating a contraction cycle detection loop routine as shown in FIG. 6.

Upon entering the contraction cycle detection routine of FIG. 7, the microcontroller, at block 180, determines whether the relax flag has been set or not. The relax flag indicates that the output of the neuro-muscular stimulation signal generator is in an idle period such as shown at 59 in FIG. 3. The channel sequencer 10 detects the idle period when a predefined length of time, such as one second, passes without the sequencer 10 seeing a pulse output from the signal generator 12. The predefined length of time is preferable greater than the inter-pulse time in a contraction cycle. However, in an alternative embodiment, the relax flag may be set on a trailing edge of a contraction cycle pulse or the like to cause the device to switch between pulses instead of during the idle period between contraction cycles. Once the microcontroller determines at block 180 that the relax flag has been set, the microcontroller proceeds to block 182 to determine whether a Pausereq flag has been set. The Pausereq flag will be set when the pause button has been actuated for a sufficient period of time. If the Pausereq flag has not been set, the microcontroller proceeds from block 182 to block 184 to determine whether the Pause flag is set. The Pause flag will be set when the device is in the pause mode. If neither the Pausereq flag or the Pause flag have been set, the microcontroller at block 186 determines whether the flag bankAdone has been set. If the bankAdone flag has been set, the microcontroller determines whether the bankBdone flag has been set at block 188 and if so, the microcontroller powers down the device at block 190. If at least one of the bankAdone or bankBdone flags has not been set, the microcontroller proceeds to block 192 to determine whether the switchbankA flag has been set, for example at block 148 during the normal mode initialization. If this flag has been set as determined at block 192, the microcontroller, at block 194, activates the current channel, chanA. Thereafter, at block 196, the microcontroller clears the switchbankA flag at block 196 and proceeds to block 198 to determine whether the switchbankB flag has been set. If the switchbankB flag has been set for example, at block 162, the microcontroller activates the current channel in bankB, chanB at block 200. At block 202, the microcontroller clears the switchbankB flag and the routine returns to block 180. As should be apparent, this routine controls the time at which the sequencer 10 switches from one output channel to the next output channel in the bank sequence so that the switch occurs during an idle period 59.

If the microcontroller determines at block 182 that the pause button has been actuated indicating that the Pausereq flag is set, the microcontroller proceeds to block 204 to determine whether the Pause flag has been set. If not, the microcontroller at block 206 deactivates all of the channels and at block 208 changes the indicator light 37 on the channel sequencer 10 to indicate that the device is currently in a pause state. At block 210, the microcontroller sets the Pause flag to indicate that the device is currently in the pause state. If the microcontroller determines at block 204 that the Pause flag is set, the microcontroller at 212 determines whether the bankAdone flag is set and if so, the microcontroller determines whether the bankBdone flag has been set at block 214. If both flags are set, the device is powered down at block 216. If at block 182, it is determined that the Pausereq flag is not set, but at block 184 it is determined that the Pause flag is set, the microcontroller proceeds to block 218 to clear the Pause flag indicating that the device is leaving the pause state. Thereafter, at block 220, the microcontroller reactivates all of the channels so that the channel sequencer can continue operation.

Figure 8:
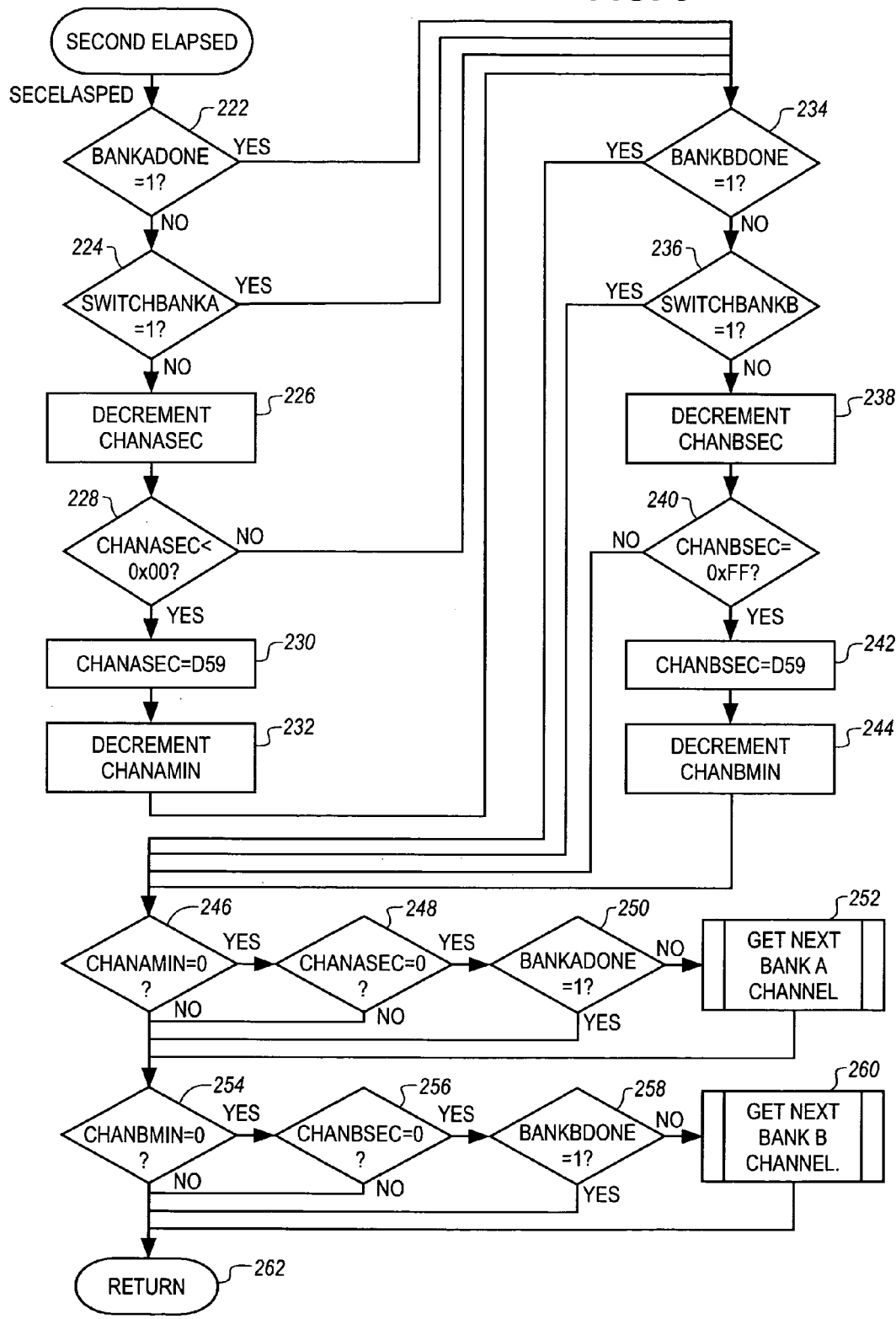
FIG. 8 is a flow chart illustrating a normal mode routine.
Figure 12:
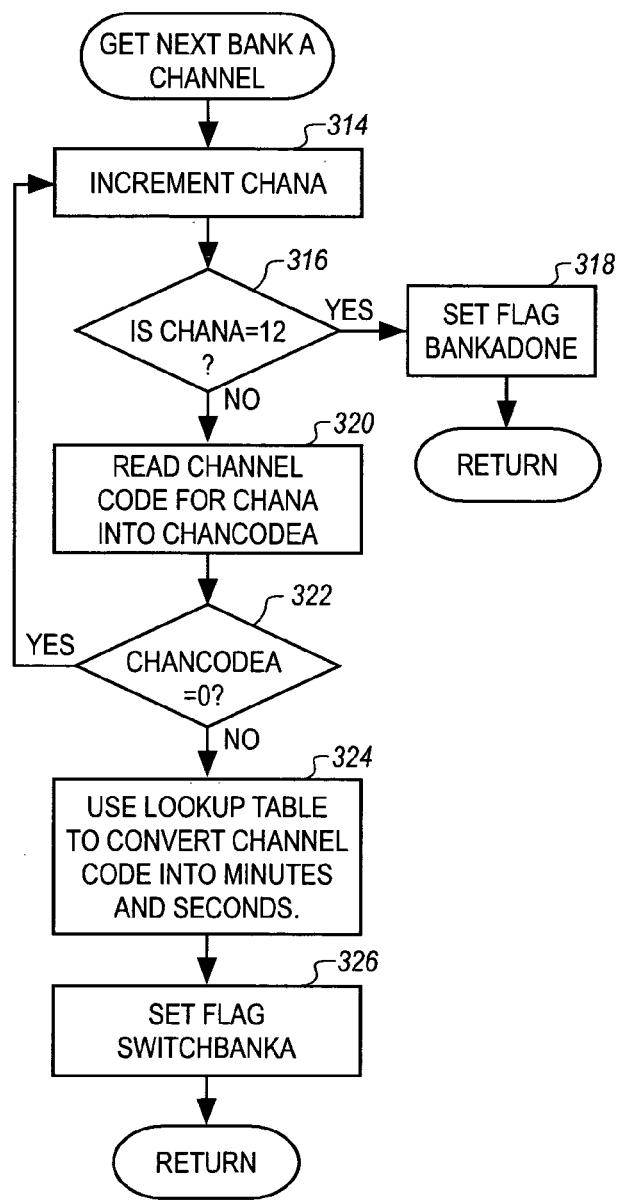
FIG. 12 is a flow chart illustrating a routine to get the time periods associated with a first bank of channels.

FIG. 8 illustrates a normal mode routine implemented after each second has elapsed. At block 222, the microcontroller determines whether the bankAdone flag has been set such that it is equal to 1 and if not, the microcontroller proceeds to block 224 to determine whether the switchbankA flag has been set so as to be equal to 1. If the current channel has just been activated such that the switchbankA flag has been cleared at block 196, for example, the microcontroller will proceed from block 224 to block 226. At block 226, the microcontroller decrements chanAsec which contains the seconds remaining for the current bank A channel. If the microcontroller determines at block 228 that there are no remaining seconds, the microcontroller proceeds to block 230 and 232 to decrement the minutes. More particularly, at block 230, the microcontroller resets chanAsec to a value representing 59 seconds and at block 232, the microcontroller decrements chanAmin to the number of minutes remaining for the current bank A channel. From block 232, the microprocessor proceeds to block 234 to similarly decrement the seconds and minutes for the current bank B channel. More particularly, at block 234, the microcontroller determines whether the bankBdone flag has been set and if not, at block 236, the microcontroller determines whether the switchbankB flag has been set. If not, the microcontroller decrements chanBsec at block 238. At block 240, the microcontroller determines whether there are any seconds left in chanBsec and if not, at block 242 chanAsec is set equal to a value representing 59 seconds and at block 244, the microcontroller decrements chanBmin. The microcontroller than proceeds to block 246 and 248 to respectively determine whether chanAmin and chanAsec are set equal to 0. If so, at block 250, the microcontroller determines whether the bankAdone flag has been set indicating that all of the bank A output channels have been finished. If the bankAdone flag is not set, the microcontroller at block 252 gets the next bank A channel as illustrated in FIG. 12 discussed below. At blocks 254 and 256 the microcontroller respectively determines whether chanBmin and chanBsec are set equal to 0. If so, at block 258, the microcontroller determines whether the bankBdone flag is set and if not, the microcontroller proceeds to block 260. At block 260, the microcontroller implements the get next bank B channel routine as depicted in FIG. 13. Thereafter, the microcontroller returns at block 262.

Figure 9:
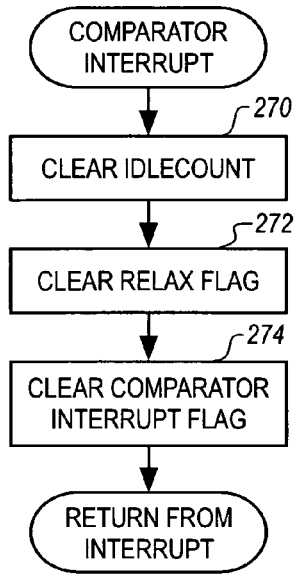
FIG. 9 is a flow chart illustrating a comparator interrupt routine.

Whenever the channel sequencer 10 receives a pulse from the neuro-muscular stimulation signal generator 12, an interrupt is generated which causes the microcontroller to implement the routine depicted in FIG. 9. At block 270 of FIG. 9, the microcontroller clears the idle count and at block 272 clears the relax flag so that the relax flag will not be set until the predefined time, such as 1 second, passes without a pulse from the signal generator being seen. At block 274, the microcontroller also clears the comparator interrupt flag and thereafter, the microcontroller returns from servicing the interrupt.

Figure 10:
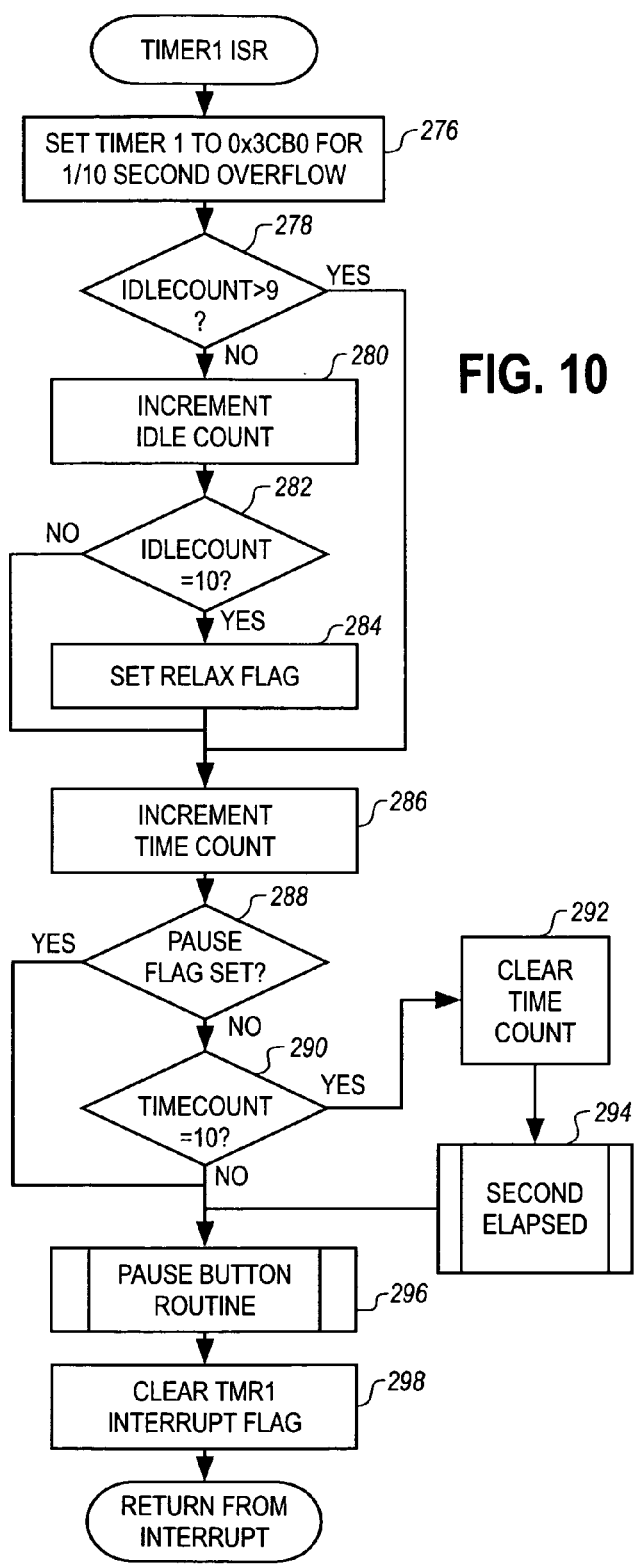
FIG. 10 is a flow chart illustrating a timer interrupt service routine.

A timer interrupt service routine, depicted in FIG. 10 is entered whenever a timer interrupt is generated which, for example, may be every 0.1 sec. Upon entering this routine, the microcontroller at block 276 sets a timer1 to 0x3CB0 for 0.1 second overflow. At block 278, the microcontroller determines whether the idle count is greater than 9 so as to determine whether the signal generator 10 is not turned on. If the idle count is not greater than 9, the microcontroller at block 280 increments the idle count and at block 282 determines whether the idle count is equal to 10. If so, the microcontroller at block 284 sets the relax flag and at block 286 increments timecount which counts up to ten 0.1 sec. intervals to find when one second has elapsed. At block 288, the microcontroller determines whether the pause flag is set and if not, the microcontroller at 290 determines whether timecount is equal to 10. Block 288 keeps the second elapsed routine at 294 from running so that the timers for the channels are not decremented. If timecount is equal to 10, the microcontroller proceeds to block 292 to clear timecount. Thereafter, at block 294, the microcontroller executes the second elapsed routine as depicted in FIG. 8. At block 296, the microcontroller enters the pause button routine as discussed below with reference to FIG. 14. Thereafter, at block 298 the microcontroller clears the timer1 interrupt flag and returns from servicing the timer interrupt.

Figure 11:
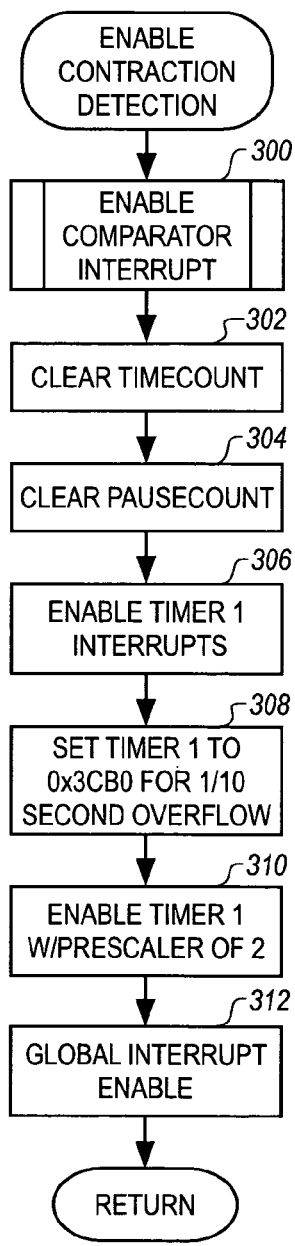
FIG. 11 is a flow chart illustrating an enable contraction detection routine.

The microcontroller enters the enable contraction detection routine depicted in FIG. 11 from block 174 of FIG. 6 wherein the routine is depicted. At block 300 of FIG. 11, the microcontroller enables the comparator interrupts. Thereafter, at blocks 302 and 304 respectively, the microcontroller clears timecount and clears pausecount. At block 306, the microcontroller enables the timer1 interrupts and at block 308 sets the timer1 to 0x3CB0 for ¹⁄₁₀ sec. overflow. The microcontroller then enables timer1 with a prescaler value of 2 at block 310. At block 312, the microcontroller enables a global interrupt and thereafter returns from the routine of FIG. 11.

FIGS. 12 and 13 respectively depict the get next bankA channel routine and get next bankB channel routine entered from respective blocks 252 and 260 of FIG. 8. Upon entering the get next bankA channel routine, the microcontroller at block 314 increments chanA. At block 316, the microcontroller determines whether the current channel, chanA is equal to 12 and if so, sets the bankAdone flag at block 318. If the current channel, chanA is not equal to 12, the microcontroller proceeds from block 316 to block 320. At block 320, the microcontroller reads the channel code representing the time period during which the current channel chanA is to be active into chancodeA. At block 322, the microcontroller determines whether chancodeA is equal to 0. If so, the microcontroller returns to block 314 to increment chanA to the next channel. If the microcontroller 322 determines that chancode A is not equal to 0 indicating that the current channel, chanA, has not been disabled, the microcontroller proceeds to block 324 to use a look up table to convert the time period channel code for chanA into minutes and seconds. Thereafter, at block 326, the microcontroller sets the switchbankA flag. Upon entering the get next bankB channel routine as depicted in FIG. 14, the microcontroller at block 328 increments chanB. At block 330, the microcontroller determines whether chanB is equal to 24 and if so, at block 332 sets the bankBdone flag. If the current channel, chanB, is not equal to 24, the microcontroller proceeds from block 330 to block 334. At block 334, the microcontroller reads the channel code representing the time period for which the current output channel, chanB, is to be active into chancodeB. The microcontroller then determines at block 336 whether chancodeB is equal to 0 indicating that the current output channel is disabled and if so, returns to block 328. If chancodeB is not equal to 0, the microcontroller proceeds from block 336 to block 338 to use the look up table to convert the channel code into minutes and seconds. At block 340, the microcontroller sets the flag switchbankB and thereafter returns.

Upon entering the pause button routine, depicted in FIG. 14, the microcontroller at block 342 determines whether the pause button has been pressed. If not, the microcontroller at block 344 clears the pause-count and returns. If the pause button has been pressed, the microcontroller proceeds from block 342 to block 346 to increment pausecount. Thereafter, at block 348, the microcontroller determines whether pausecount is equal to 0. If so, the microcontroller at block 350 sets pausecount to 0xFF to keep it from wrapping around. If the microcontroller determines at block 348 that pausecount is not equal to 0, the microcontroller determines at block 352 whether pausecount equals 2 which indicates that the user has held the pause button for 0.2 seconds so as to initiate the pause state. If so, the microcontroller at block 354 toggles the pausereq flag. If the microcontroller determines at block 352 that pausecount is not equal to 5, the microcontroller proceeds to block 356 to determine whether pausecount equals 20. If pausecount equals 20 then the user has held the pause button for at least 2.0 seconds so as to indicate that the device is to be powered down. If pausecount equals 20, the microcontroller at block 360 sets both the bankAdone and bankBdone flags to cause the device to power down. From blocks 356 or 360 the microcontroller returns to the calling routine.

The microcontroller 400 for the channel sequencer 10 as shown in FIG. 15, may be any type of microcontroller including a microprocessor and memory. The microcontroller shown is a PIC16F876A/SS. The positive lead of the neuro-muscular stimulation signals 402 and 403 from the first and second output channels of the signal generator 10 are coupled to the microcontroller 400 on respective lines 404 and 405 via resistors R14 and R15. The negative leads of the neuro-muscular stimulation signals 406, 407 from the first and second output channels of the signal generator 10 are tied to ground via resistors R16 and R17. A clock 408 is coupled to the microcontroller 400 via lines 410 and 412. The pause and power off button 35 is coupled to the microcontroller 400 via the line 414 and the respective status LEDs 37 and 39 are coupled to the microcontroller on respective lines 416, 418 via resistors R3 and R1.

Figure 16:
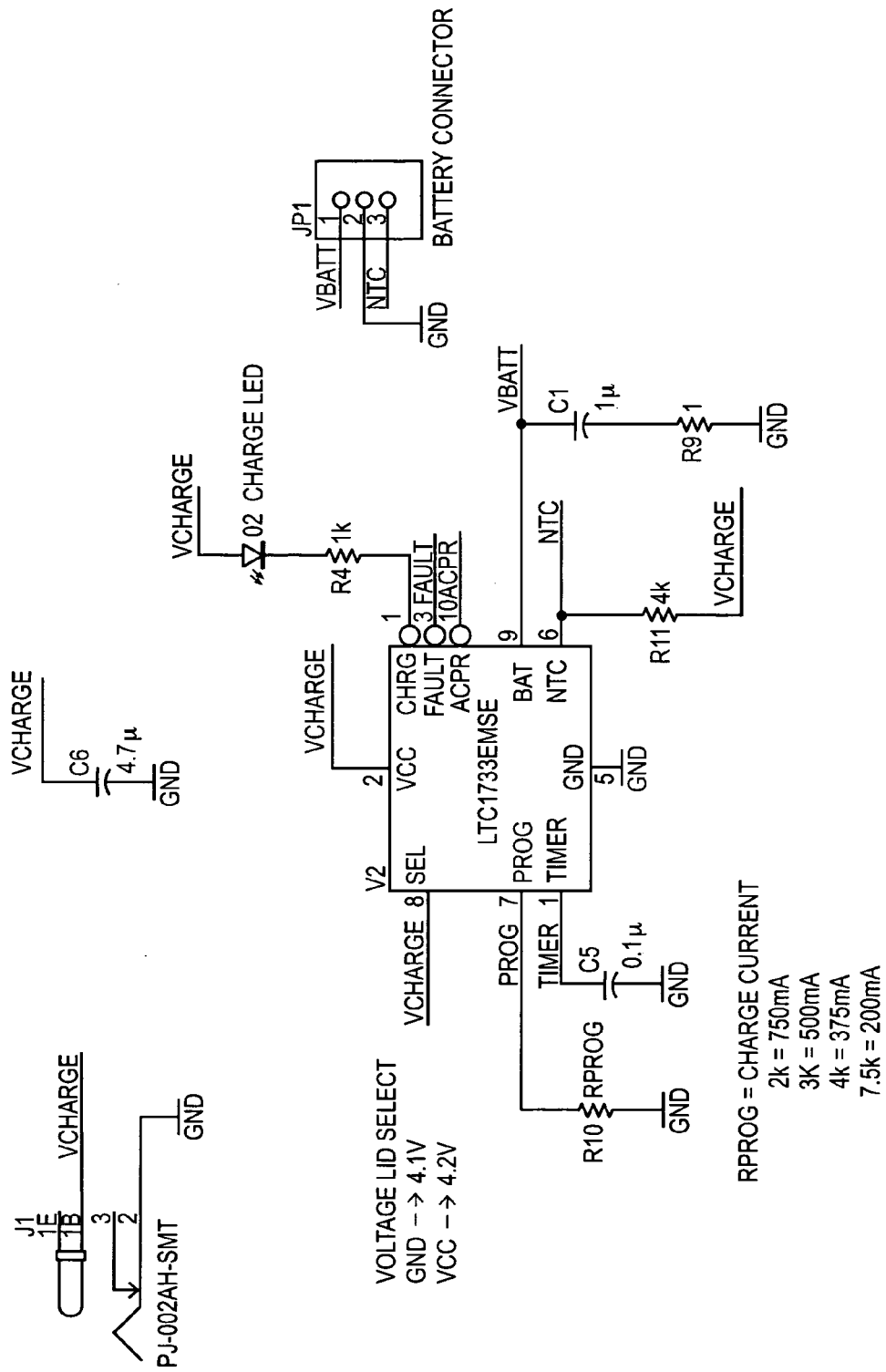
FIG. 16 is a schematic diagram of a lithium ion battery charge circuit.
Figure 17:
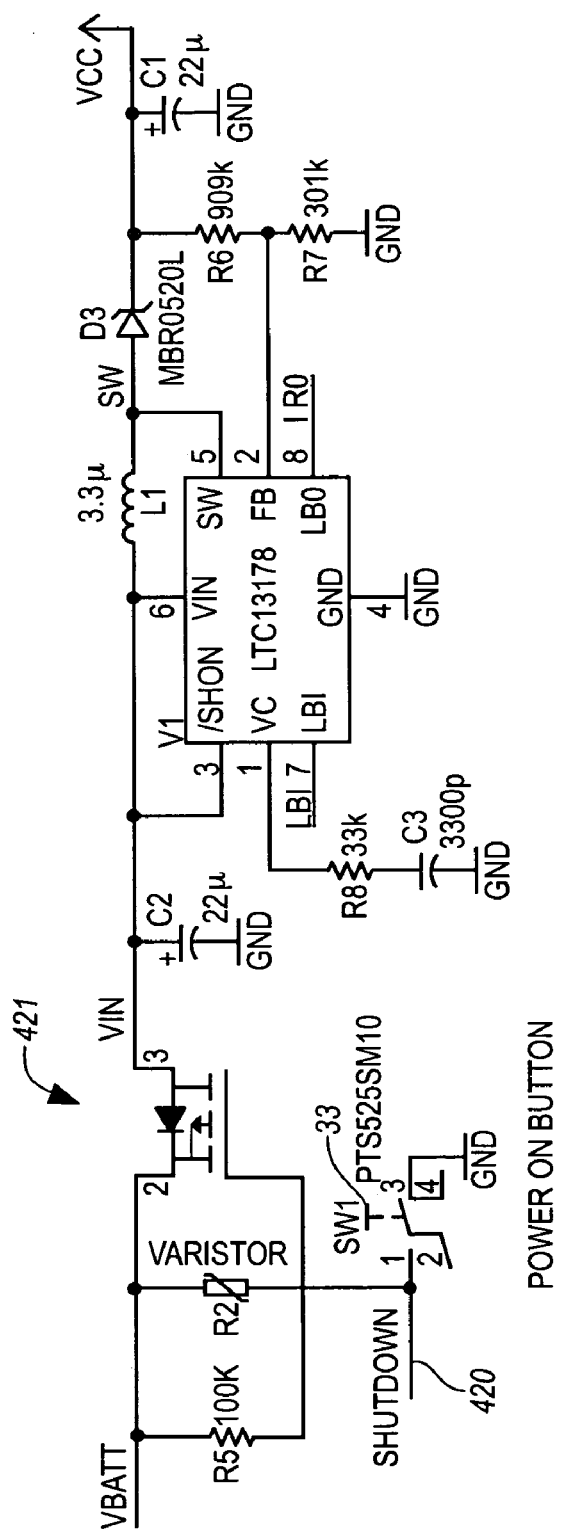
FIG. 17 is a schematic diagram of a lithium ion boost converter circuit.
Figure 18:
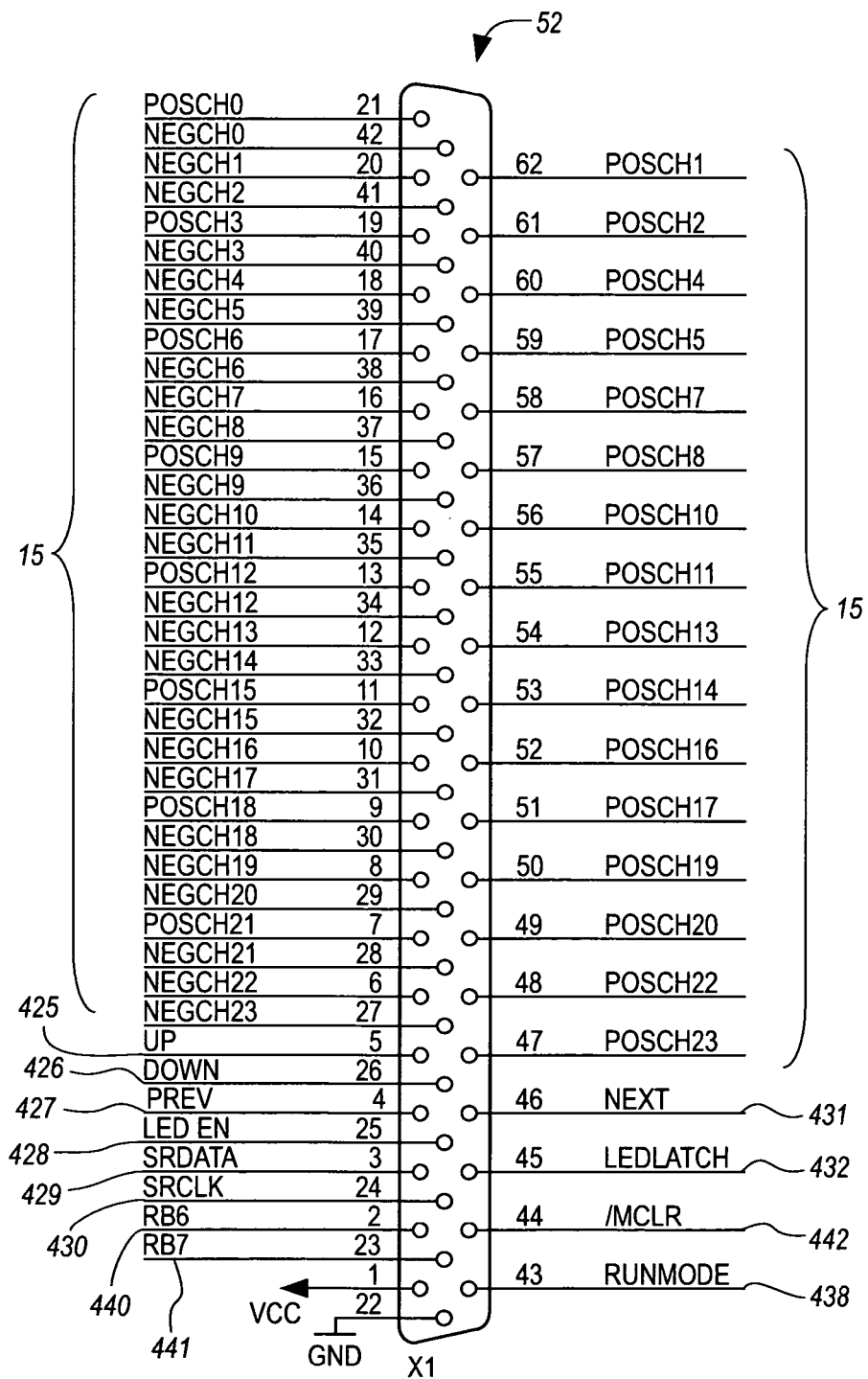
FIG. 18 is a schematic diagram illustrating the connector pin inputs/outputs of the channel sequencer of FIGS. 1 and 2.

The channel sequencer 10 of the present invention is preferably powered by a lithium ion battery. A suitable charge circuit for the lithium ion battery is depicted in FIG. 16. A boost converter circuit for the lithium ion battery is shown in FIG. 17 wherein the circuit steps up the voltage for the channel sequencer relays discussed below. When the power on button 33 is pressed, the microcontroller holds line 420 low when the user releases the button 33 to maintain power. The microcontroller 400 powers down the sequencer by releasing the line 420 so that the power MOSFET 421 is turned off. The connector 52 with the twenty-four output channels 15 of the channel sequencer 10 is illustrated in FIG. 18. For each of the 24 output channels there is a connection 422 and 424 for the respective positive and negative leads of the output channel. The connections 425–432 are used to communicate with the programmer 16. The line 438 of the connector 52 is pulled to ground when the programmer 16 is coupled to the channel sequencer so as to indicate to the microcontroller 400 that the device is operating in the programming mode. The connections 440–442 allow the firmware of the microcontroller 400 to be upgraded or changed in the field.

Figure 19:
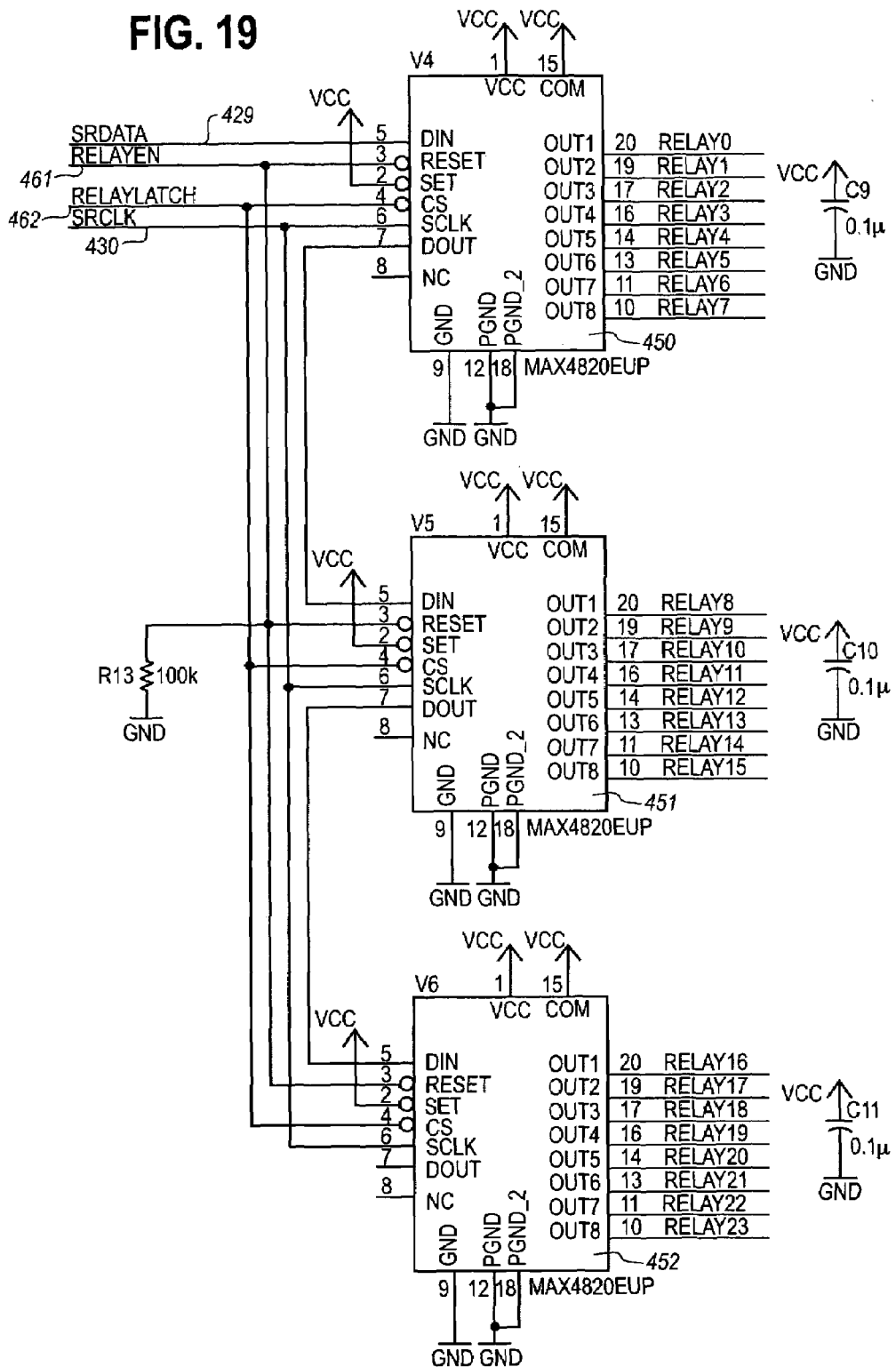
FIG. 19 is a schematic diagram of a relay driver circuit for the channel sequencer.
Figure 20:
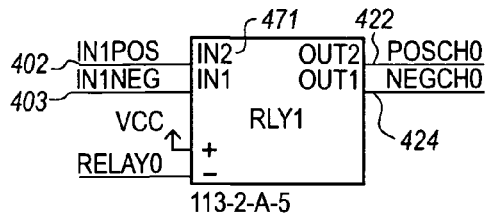
FIG. 20 is an illustration of the relays for the first bank of output channels of the sequencer.
Figure 20:
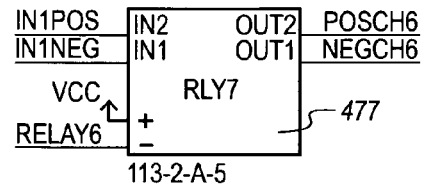
Figure 20:
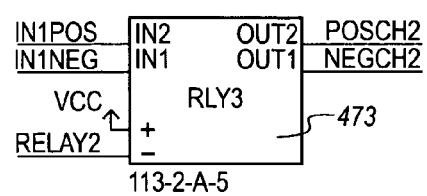
Figure 20:
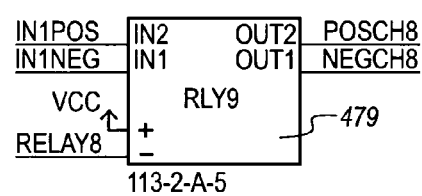
Figure 20:
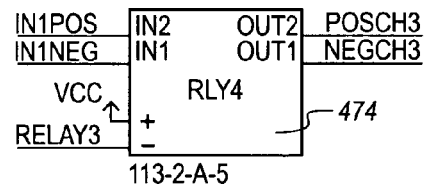
Figure 20:
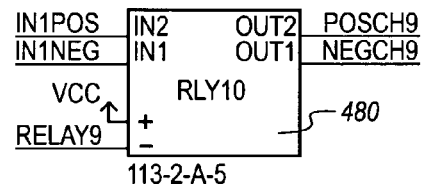
Figure 20:
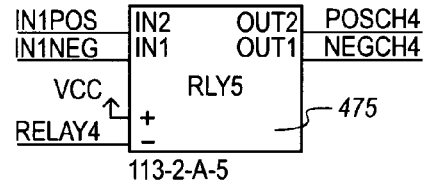
Figure 20:
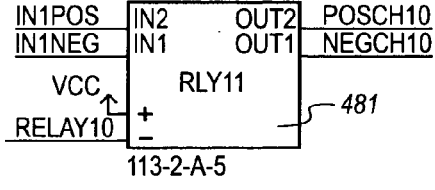
Figure 20:
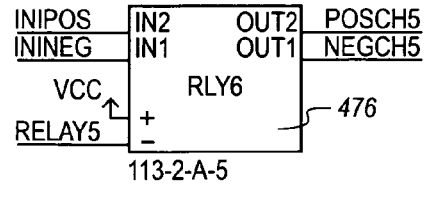
Figure 20:
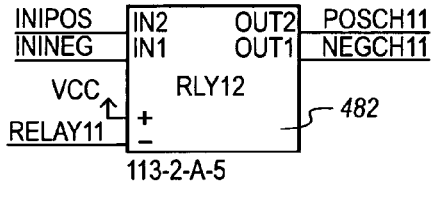
Figure 20:
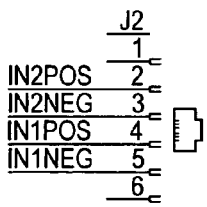
Figure 21:
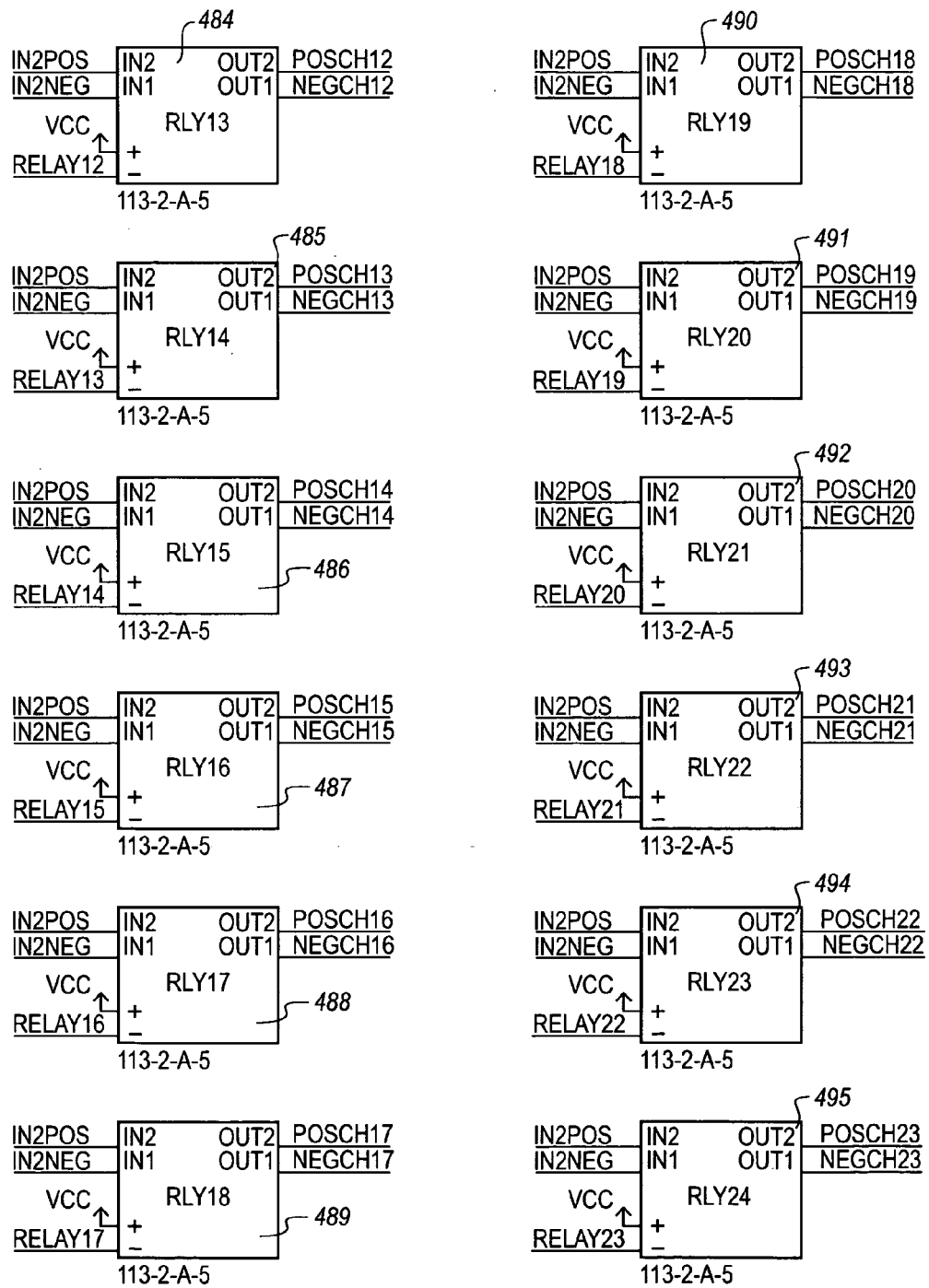
FIG. 21 is an illustration of the relays for the second bank of output channels of the sequencer.

FIG. 19 illustrates the drive circuit for the 12 bankA relays 471–482 shown in FIG. 20 and for the 12 bankB relays 484–495 shown in FIG. 21. The relay drive circuit includes shift registers 450, 451 and 452 with inductive kickback suppression that are coupled to the microcontroller 400 via lines 429, 430, 461 and 462. The 24 outputs of the shift registers 450–452 are coupled to respective inputs of the relays 471–482 and 484–495. Each relay, when actuated by the microcontroller via the relay drive circuit of FIG. 19, couples the positive and negative leads 402 and 403 of the stimulation signal generated by the signal generator 12 to the positive and negative outputs 422 and 424 of the connector 52 for the respective output channel 15.

Figure 22:
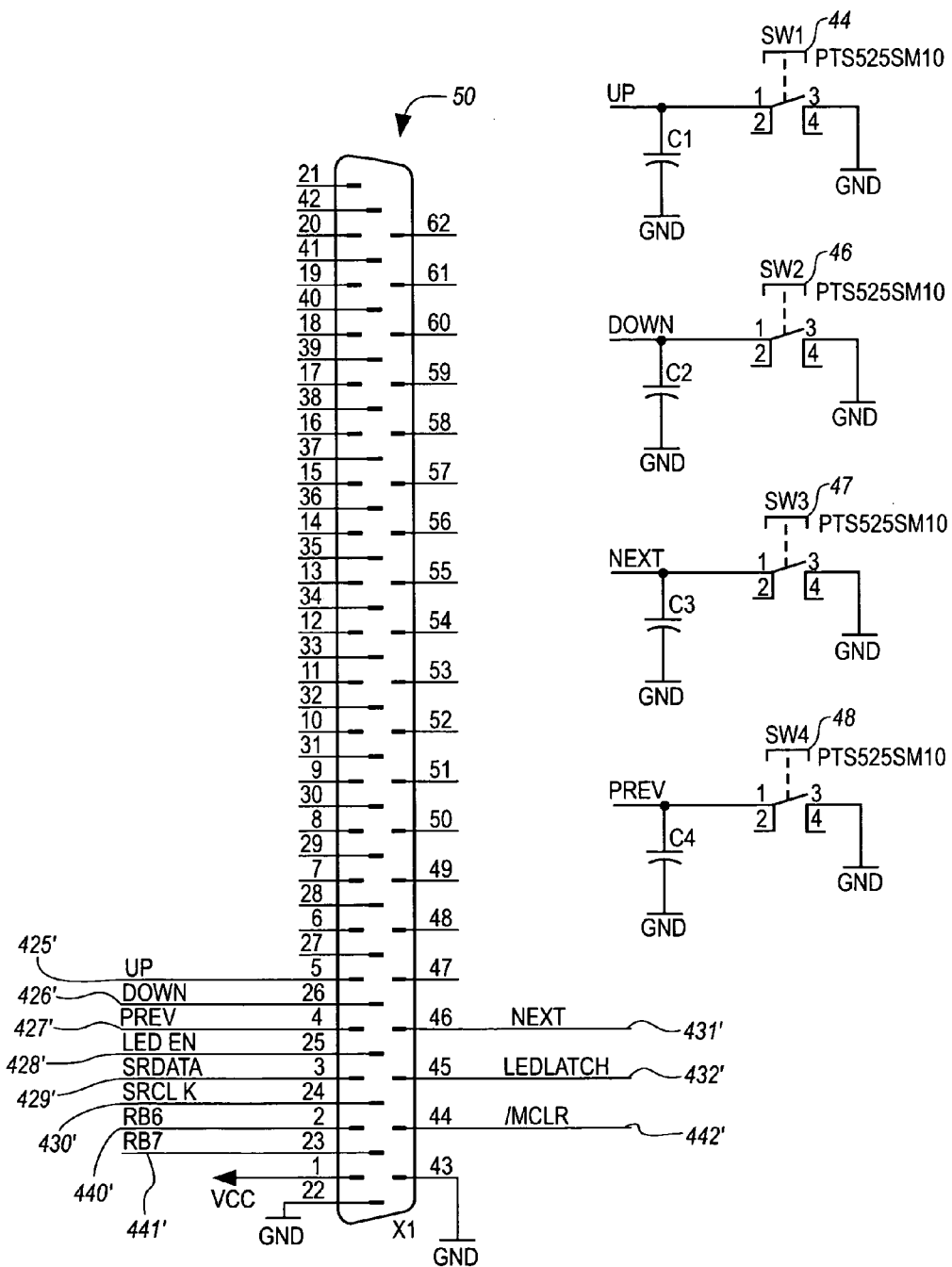
FIG. 22 is an illustration of the connector pins and buttons for the programmer module.
Figure 23B:
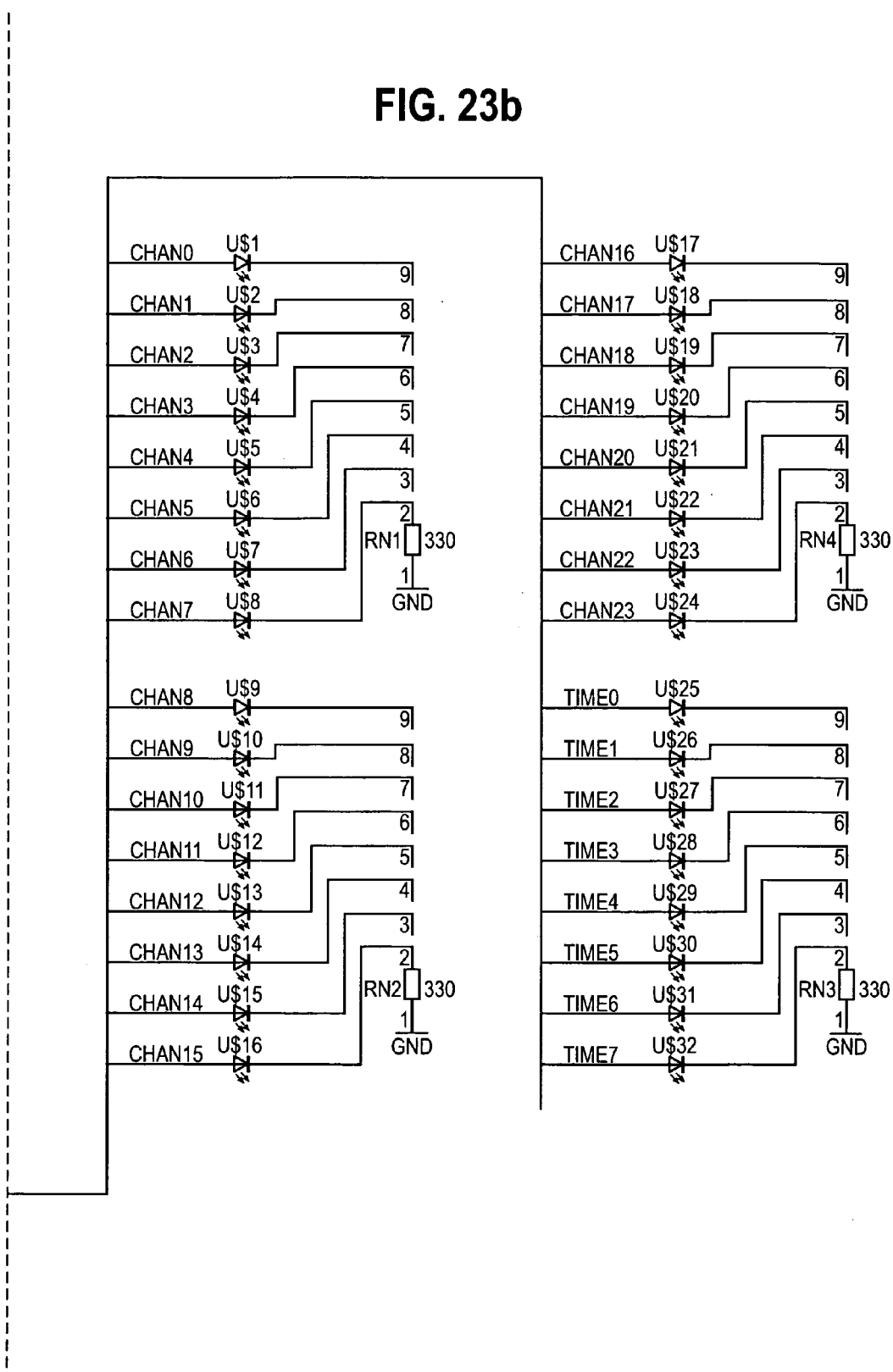
FIG. 23 is an illustration of the programmer LED driver circuitry of the programmer module.

FIG. 22 illustrates the programmer 16 control buttons 44, 46, 47 and 48 which are respectively coupled via the programmer connector 50 connections 425', 426', 431' and 427' to respective connections 425, 426, 431 and 427 of the connector 52 of the channel sequencer 10. The connections 428'–430', 432', and 440'–442' of the programmer 16 connector 50 are coupled to respective connectors 428–430, 432 and 440–442 of the channel sequencer 10 connector 15 when the two units 16 and 10 are mated. The drive circuitry for the LEDs 40, 42 and 44 is illustrated in FIG. 23.

Many modifications and variations of the present invention are possible in light of the above teachings. Thus, it is to be understood that, within the scope of the appended claims, the invention may be practiced otherwise than as described hereinabove.

What is claimed and desired to be secured by Letters Patent is:

1. A portable neuro-muscular stimulation system comprising:
   a portable programmable patient activated device including a neuro-muscular stimulation signal generator, a channel sequencer having at least six output channels each capable of being connected to a pair of electrodes, the channel sequencer coupling the stimulation signal generator to selected output channels for a period of time in a predetermined sequence to provide a therapy; and
   a programmer capable of communicating with the patient activated device to program a period of time during which the stimulation signal is to be coupled to a selected output channel such that the patient activated device is capable of being programmed with different time periods for at least two different output channels.

2. A portable neuro-muscular stimulation system as recited in claim 1 wherein each of the time periods during which the stimulation signal is coupled to a selected output channel is individually programmable for each output channel.

3. A portable neuro-muscular stimulation system as recited in claim 1 wherein the channel sequencer couples a stimulation signal to at least two output channels for respective periods of time that overlap.

4. A portable neuro-muscular stimulation system as recited in claim 1 wherein the sequencer output channels are divided into at least two groups that are simultaneously active during at least a portion of the therapy.

5. A portable neuro-muscular stimulation system as recited in claim 1 wherein the programmer provides a visual indication identifying the output channel currently being programmed.

6. A portable neuro-muscular stimulation system as recited in claim 1 including a light emitting diode associated with each output channel to provide a visual indication.

7. A portable neuro-muscular stimulation system as recited in claim 1 wherein the programmer provides a visual indication of a selected period of time to be programmed for coupling the stimulation signal to an output channel.

8. A portable neuro-muscular stimulation system as recited in claim 1 wherein the patient activated device provides feedback to the user regarding the current stage of the therapy.

9. A portable neuro-muscular stimulation system comprising:
   a signal generator for providing at least one neuro-muscular stimulation signal; and
   a channel sequencer having six or more output channels, each output channel being coupled to a pair of electrodes, the channel sequencer coupling the stimulation signal to selected output channels in a predetermined sequence for a period of time that is individually programmable for the respective output channel, the channel sequencer automatically switching the stimulation signal from a current output channel to a next output channel in the sequence in response to the expiration of the programmed period of time associated with the current output channel.

10. A portable neuro-muscular stimulation system as recited in claim 9 wherein the electrodes have a diameter of one inch or less.

11. A portable neuro-muscular stimulation system as recited in claim 9 wherein the signal generator provides a second neuro-muscular stimulation signal and the channel sequencer couples the one stimulation signal and the second stimulation signal to different output channels such that two channel outputs are active at the same time during at least a portion of a therapy.

12. A portable neuro-muscular stimulation system as recited in claim 11 wherein each of the neuro-muscular stimulation signals has a first cycle portion during which a plurality of pulses are generated followed by a second cycle portion during which no pulses are generated, the second cycle portion being greater than the time between pulses generated during the first cycle portion and wherein the first cycle portions of the stimulation signals substantially overlap.

13. A portable neuro-muscular stimulation system as recited in claim 12 wherein the pulses generated during the first cycle portion of the first stimulation signal are offset from the pulses generated during the first cycle portion of the second stimulation signal.

14. A portable neuro-muscular stimulation system as recited in claim 9 wherein the neuro-muscular stimulation signal has a first cycle portion during which one or more pulses are generated and a second cycle portion during which no pulses are generated for a period of time and wherein the channel sequencer automatically switches channels during the second cycle.

15. A portable neuro-muscular stimulation system as recited in claim 9 wherein the diameter of each facial electrode is approximately three quarters of an inch.

16. A portable neuro-muscular stimulation system as recited in claim 9 wherein the signal generator and channel sequencer are contained in one housing.

17. A portable neuro-muscular stimulation system as recited in claim 9 wherein the signal generator and the channel sequencer are contained in separate housings configured to that mate.

18. A system to adapt a neuro-muscular stimulator generating at least one neuro-muscular stimulation signal on at least one stimulator output channel, the system being capable of automatically treating a larger number of neuro-muscular locations comprising:

a portable channel sequencer to couple a neuro-muscular stimulation signal received from the neuro-muscular stimulator to a number of sequencer output channels in a predetermined sequence wherein the number of sequencer output channels is greater than the number of stimulator output channels; and a programmer capable of communicating with the channel sequencer to program a period of time during which a stimulation signal is to be coupled to a selected output channel such that the channel sequencer is capable of being programmed with different time periods for at least two different output channels.

19. A portable neuro-muscular stimulation system as recited in claim 18 wherein each period of time during which the stimulation signal is coupled to a selected output channel is individually programmable for each output channel.

20. A portable neuro-muscular stimulation system as recited in claim 18 wherein the channel sequencer couples a stimulation signal to at least two output channels for respective periods of time that overlap.

21. A portable neuro-muscular stimulation system as recited in claim 18 wherein the sequencer output channels are divided into at least two groups that are simultaneously active during at least a portion of a therapy.

22. A portable neuro-muscular stimulation system as recited in claim 18 wherein the programmer provides a visual indication identifying the output channel currently being programmed.

23. A portable neuro-muscular stimulation system as recited in claim 18 including a light emitting diode associated with each output channel to provide a the visual indication.

24. A portable neuro-muscular stimulation system as recited in claim 18 wherein the programmer provides a visual indication of a selected period of time to be programmed for coupling the stimulation signal to an output channel.

25. A portable neuro-muscular stimulation toning system as recited in claim 18 wherein the patient activated device provides feedback to a user regarding the current stage of a therapy.

26. An adapter for a neuro-muscular electrical stimulator that generates a neuro-muscular stimulation signal on at least one output channel to adapt the stimulator for automatically treating a larger number of neuro-muscular locations comprising:

a programmable channel sequencer having a portable housing with an input that receives the stimulation signal output from the neuro-muscular electrical stimulator and having a plurality of channel outputs greater in number than the channel outputs of the neuro-muscular electrical stimulator, each of the sequencer channel outputs being capable of providing an output stimulation signal to a pair of electrodes, the channel sequencer coupling the stimulation signal on one output channel of the neuro-muscular electrical stimulator to a selected group of channel outputs of the channel sequencer in a predetermined sequence wherein a time period during which the stimulation signal on the one output channel of the neuro-muscular electrical stimulator is coupled to a sequencer output channel in the selected group is individually programmable, the channel sequencer automatically switching the stimulation signal from a current sequencer channel output to a next selected channel output in the sequence in response to the expiration of the programmable period of time associated with the current sequencer channel output.

27. An adaptor for a neuro-muscular electrical stimulator as recited in claim 26 wherein the channel sequencer includes at least six channel outputs, and further including a pair of electrodes coupled to each of the channel outputs, the electrodes having a diameter of one inch or less.

28. An adaptor for a neuro-muscular electrical stimulator as recited in claim 26 wherein the neuro-muscular electrical stimulator generates a first muscle stimulation signal and a second muscle stimulation signal and the channel sequencer couples the first and second signals to different sequencer output channels such that the time periods that different sequencer outputs are active substantially overlaps.

29. An adaptor for a neuro-muscular electrical stimulator as recited in claim 28 wherein the time periods during which the first and second stimulation signals are coupled to the different sequencer channel outputs may be programmable to the same or different periods.

30. An adaptor for a neuro-muscular electrical stimulator as recited in claim 26 wherein the neuro-muscular electrical stimulator generates a first muscle stimulation signal and a second muscle stimulation signal and the channel sequencer couples the first signal to a first group of sequencer output channels in a predetermined sequence and in a parallel couples the second signal to a second group of sequencer output channels in another predetermined sequence.

31. An adaptor for a neuro-muscular electrical stimulator as recited in claim 30 wherein a time period during which the first signal is coupled to a sequencer output channel in the first group and a time period during which the second signal is coupled to a sequencer output channel in the second group are individually programmable and the channel sequencer couples the first stimulation signal to a sequencer output channel in the first group during a time period that overlaps at least in part with a time period that the channel sequencer couples the second stimulation signal to a sequencer output channel in the second group.

32. An adaptor for a neuro-muscular electrical stimulator as recited in claim 30 wherein a time period during which the first stimulation signal is coupled to a sequencer output channel in the first group is programmable and a time period during which the second stimulation signal is coupled to a sequencer output channel in the second group is automatically set to a time period corresponding to the time period programmed for the output channel in the first group.

33. An adaptor for a neuro-muscular electrical stimulator as recited in claim 26 wherein the stimulation signal generated by the neuro-muscular electrical stimulator has a first cycle portion during which one or more pulses are generated and a second cycle portion during which no pulses are generated for a period of time and wherein the channel sequencer automatically switches output channels during the second cycle portion.

34. An adaptor for a neuro-muscular electrical stimulator as recited in claim 26 wherein the channel sequencer includes at least six channel outputs, and further including a pair of electrodes coupled to each of the channel outputs, the electrodes having a diameter of three quarters of an inch.

35. An adaptor for a neuro-muscular electrical stimulator as recited in claim 26 wherein the housing of the channel sequencer is configured to mate with a housing of the neuro-muscular electrical stimulator so as to form one portable unit.

* * * * *